US011990209B2

(12) United States Patent
Lu et al.

(10) Patent No.: US 11,990,209 B2
(45) Date of Patent: May 21, 2024

(54) IDENTIFICATION OF INSTANCE-SPECIFIC SOMATIC GENOME ALTERATIONS WITH FUNCTIONAL IMPACT

(71) Applicant: University of Pittsburgh—Of the Commonwealth System of Higher Education, Pittsburgh, PA (US)

(72) Inventors: Xinghua Lu, Pittsburgh, PA (US); Gregory Cooper, Pittsburgh, PA (US); Chunhui Cai, Pittsburgh, PA (US); Shyam Visweswaran, Pittsburgh, PA (US)

(73) Assignee: UNIVERSITY OF PITTSBURGH—OF THE COMMONWEALTH SYSTEM OF HIGHER EDUCAT, Pittsburgh, PA (US)

( * ) Notice: Subject to any disclaimer, the term of this patent is extended or adjusted under 35 U.S.C. 154(b) by 975 days.

(21) Appl. No.: 16/349,192

(22) PCT Filed: Nov. 13, 2017

(86) PCT No.: PCT/US2017/061373
§ 371 (c)(1),
(2) Date: May 10, 2019

(87) PCT Pub. No.: WO2018/089927
PCT Pub. Date: May 17, 2018

(65) Prior Publication Data
US 2019/0287651 A1  Sep. 19, 2019

Related U.S. Application Data

(60) Provisional application No. 62/420,936, filed on Nov. 11, 2016.

(51) Int. Cl.
*G16B 20/20* (2019.01)
*G16B 20/10* (2019.01)
(Continued)

(52) U.S. Cl.
CPC ............. *G16B 40/20* (2019.02); *G16B 20/10* (2019.02); *G16B 20/20* (2019.02); *G16B 25/00* (2019.02); *G16B 40/00* (2019.02)

(58) Field of Classification Search
CPC ......... G16B 20/20; G16B 25/00; G16B 40/00
See application file for complete search history.

(56) References Cited

U.S. PATENT DOCUMENTS

| | | | | |
|---|---|---|---|---|
| 2013/0097125 A1* | 4/2013 | Marvasti | ................ | G06F 16/90 707/E17.002 |
| 2013/0245959 A1* | 9/2013 | Bhavnani | ............... | G16B 45/00 702/19 |
| 2017/0242958 A1* | 8/2017 | Brown | .................. | G16B 20/20 |

FOREIGN PATENT DOCUMENTS

| | | |
|---|---|---|
| EP | 2549399 | 1/2013 |
| WO | WO 2016/011558 | 1/2016 |
| WO | WO 2016/154493 | 9/2016 |

OTHER PUBLICATIONS

Ding, J., McConechy, M.K., Horlings, H.M., Ha, G., Chun Chan, F., Funnell, T., Mullaly, S.C., Reimand, J., Bashashati, A., Bader, G.D. and Huntsman, D., 2015. Systematic analysis of somatic mutations impacting gene expression in 12 tumour types. Nature communications, 6(1), pp. 1-13. (Year: 2015).*

(Continued)

*Primary Examiner* — Olivia M. Wise
*Assistant Examiner* — Janna Nicole Schultzhaus
(74) *Attorney, Agent, or Firm* — Fish & Richardson P.C.

(57) ABSTRACT

The present application provides methods for the identification of somatic genome alterations with functional impact in the genome of a tumor. In several embodiments, the (Continued)

methods comprise generating a bipartite causal Bayesian network with maximal posterior probability including causal edges pointing from genes including somatic mutations and somatic copy number alterations in the genome of the tumor to genes having differential expression in the tumor. The methods can be used, for example, to identify driver somatic genome alterations in the genome of a tumor.

20 Claims, 16 Drawing Sheets

Specification includes a Sequence Listing.

(51) Int. Cl.
    *G16B 25/00*      (2019.01)
    *G16B 40/00*      (2019.01)
    *G16B 40/20*      (2019.01)

(56) References Cited

OTHER PUBLICATIONS

Lenburg, M.E., Liou, L.S., Gerry, N.P., Frampton, G.M., Cohen, H.T. and Christman, M.F., 2003. Previously unidentified changes in renal cell carcinoma gene expression identified by parametric analysis of microarray data. BMC cancer, 3(1), pp. 1-19. (Year: 2003).*

Amgalan, B. and Lee, H., 2015. DEOD: uncovering dominant effects of cancer-driver genes based on a partial covariance selection method. Bioinformatics, 31(15), pp. 2452-2460. (Year: 2015).*

Ding, J., McConechy, M.K., Horlings, H.M., Ha, G., Chun Chan, F., Funnell, T., Mullaly, S.C., Reimand, J., Bashashati, A., Bader, G.D. and Huntsman, D., 2015. Systematic analysis of somatic mutations impacting gene expression in 12 tumour types. Nature communications, 6(1), pp. 1-13. (Year: 2015) Supplementary Info.*

Bashashati, A., Haffari, G., Ding, J., Ha, G., Lui, K., Rosner, J., Huntsman, D.G., Caldas, C., Aparicio, S.A. and Shah, S.P. DriverNet: uncovering the impact of somatic driver mutations on transcriptional networks in cancer. Genome Biology, 13(12), pp. 1-14. (Year: 2012).*

Adamou et al., "Modeling clinician detection time of a disease outbreak due to inhalational anthrax," Advances in Disease Surveillance, 2006, 1(3): 2 pages.

Adzhubei et al., "Predicting functional effect of human missense mutations using PolyPhen-2," Curr. Protoc. Hum. Genet., Jan. 2013, 76(1):7.20.1-.41.

Aliferis et al., "A new formalism for temporal modeling in medical decision-support systems," Proc Annu Symp Comput Appl Med Care, 1995, 213-7.

Aliferis et al., "A temporal analysis of Qmr," J Am Med Inform Assoc., 1996, 3(1):79-91.

Aliferis et al., "A temporal analysis of QMR: abstracted temporal representation and reasoning and initial assessment of diagnostic performance trade-offs," Proc Annu Symp Comput Appl Med Care, 1994, 709-15.

Aliferis et al., "An evaluation of an algorithm for inductive learning of Bayesian belief networks using simulated data sets," Uncertainty Proceedings 1994, Jan. 1994, 8-14.

Aliferis et al., "Data explorer: a prototype expert system for statistical analysis," Proceedings of the Annual Symposium on Computer Application in Medical Care, 1993, 389-93.

Aliferis et al., "Representing and developing temporally abstracted knowledge as a means towards facilitating time modeling in medical decision-support systems," Computers in Biology and Medicine, Sep. 1997, 27(5):411-34.

Aliferis et al., "Temporal representation design principles: an assessment in the domain of liver transplantation," Proceedings of the AMIA Symposium, 1998, 170-4.

Ambrosino et al., "The use of misclassification costs to learn rule-based decision support models for cost-effective hospital admission strategie," Proceedings of the Annual Symposium on Computer Application in Medical Care, 1995, 304-8.

Andrews et al., "Learning high-dimensional directed acyclic graphs with mixed data-types," Proceedings of Machine Learning Research, Aug. 2019, 104:4-21.

Aronis et al., "A Bayesian approach for detecting a disease that is not being modeled," Plos One, Feb. 2020, 15(2):e0229658, 15 pages.

Aronis et al., "A Bayesian system to detect and characterize overlapping outbreaks," Journal of Biomedical Informatics, Sep. 2017, 73:171-81.

Aronis et al., "A method for detecting and characterizing multiple outbreaks of infectious diseases," Online Journal of Public Health Informatics, Mar. 2016, 8(1):e5, 1 page.

Aronis et al., "A Retrospective Study of the Effect of a Prognostic Model on the Hospital Admission Decision for Patients with Low Risk Community-acquired Pneumonia," Proceedings of the AMIA Symposium, 2000, 956.

Aronis et al., "Detecting Overlapping Outbreaks of Influenza," Online Journal of Public Health Informatics, 2017, 9(1):e14, 2 pages.

Aronis et al., "Identifying patient subgroups with simple Bayes'," Proceedings of the AMIA Symposium, 1999, 658-62.

Arora et al., "IBIZA: E-market Infrastructure for Custom-built Information Products," Information Systems Frontiers, Jan. 2000, 2(1):65-84.

Ashburner et al., "Gene ontology: tool for the unification of biology," Nature genetics, May 2000, 25(1):25-9.

Auble et al., "A prediction rule to identify low-risk patients with heart failure," Academic Emergency Medicine, Jun. 2005, 12(6):514-21.

Avali et al., "Application of bayesian logistic regression to mining biomedical data," AMIA Annual Symposium Proceedings, 2014, 2014:266-73.

Balasubramanian et al., "Selective model averaging with bayesian rule learning for predictive biomedicine," AMIA Summits on Translational Science Proceedings, 2014, 2014:17-22.

Batal et al., "A bayesian scoring technique for mining predictive and non-spurious rules," Joint European Conference on Machine Learning and Knowledge Discovery in Databases, Sep. 2012, 7524:260-76.

Batal et al., "A Pattern Mining Approach for Classifying Multivariate Temporal Data," Proceedings (IEEE Int Conf Bioinformatics Biomed), 2011, 2011:358-65.

Batal et al., "A temporal pattern mining approach for classifying electronic health record data," ACM Transactions on Intelligent Systems and Technology, 2013, 4(4):1-22.

Batal et al., "An efficient pattern mining approach for event detection in multivariate temporal data," Knowledge and Information Systems, Jan. 2016, 46(1):115-50.

Beinlich et al., "The Alarm monitoring system: A case study with two probabilistic inference techniques for belief networks," AIME 89, 1989, 247-56.

Bertrand et al., "Patient-specific driver gene prediction and risk assessment through integrated network analysis of cancer omics profiles," Nucleic Acids Research, Jan. 2015, 43(7):e44, 13 pages.

Biankin et al., "Patient-centric trials for therapeutic development in precision oncology," Nature, Oct. 2015, 526(7573):361-70.

Buchanan et al., "Creating a Software Tool for the Clinical Researcher—the IPS System," Proceedings of the AMIA Symposium, 2002, 1210.

Cadwell et al., "The effects of wild-type p53 tumor suppressor activity and mutant p53 gain-of-function on cell growth," Gene, Oct. 2001, 277(1-2):15-30.

Cai et al., "Systematic discovery of the functional impact of somatic genome alterations in individual tumors through tumor-specific causal inference," PLOS Computational Biology, Jul. 2019, 15(7):e1007088, 29 pages.

Califano et al., "Leveraging models of cell regulation and GWAS data in integrative network-based association studies," Nature genetics, Aug. 2012, 44(8):841-7.

(56) References Cited

OTHER PUBLICATIONS

Cancer Genome Atlas Network, "Comprehensive molecular portraits of human breast tumours, " Nature, Oct. 2012, 490(7418):61-70.
Carracedo et al., "The PTEN-PI3K pathway: of feedbacks and cross-talks," Oncogene, Sep. 2008, 27(41):5527-41.
Carter et al., "Cancer-specific high-throughput annotation of somatic mutations: computational prediction of driver missense mutations," Cancer Research, Aug. 2009, 69(16):6660-7.
Chang et al., "p53 regulates epithelial-mesenchymal transition and stem cell properties through modulating miRNAs," Nature Cell Biology, 2011, 13(3):317-23.
Chapman et al., "A simple algorithm for identifying negated findings and diseases in discharge summaries," Journal of Biomedical Informatics, Oct. 2001, 34(5):301-10.
Chapman et al., "Creating a text classifier to detect radiology reports describing mediastinal findings associated with inhalational anthrax and other disorders," Journal of the American Medical Informatics Association, Sep. 2003, 10(5):494-503.
Chapman et al., "Evaluation of negation phrases in narrative clinical reports," Proceedings of the AMIA Symposium, 2001, 105-9.
Chatr-Aryamontri et al., "The BioGRID interaction database: 2013 update," Nucleic acids research, Nov. 2012, 41(D1):D816-23.
Chavez et al., "A randomized approximation algorithm for probabilistic inference on Bayesian belief networks," Networks, Aug. 1990, 20(5):661-85.
Chavez et al., "An empirical evaluation of a randomized algorithm for probabilistic inference," Machine Intelligence and Pattern Recognition, Jan. 1990, 10:191-207.
Chavez et al., "Hypermedia and randomized algorithms for medical expert systems," Computer Methods and Programs in Biomedicine, May 1990, 32(1):5-16.
Chen et al., "Conceptualization of molecular findings by mining gene annotations," BMC proceedings, Dec. 2013, 7(S7):S2, 12 pages.
Chin et al., "Case-based tutoring from a medical knowledge base," Computer Methods and Programs in Biomedicine, Oct. 1989, 30(2-3):185-98.
Chudnovsky et al., ZFHX4 interacts with the NuRD core member CHD4 and regulates the glioblastoma tumor-initiating cell state, Cell Reports, Jan. 2014, 6(2):313-24.
Ciriello et al., "Emerging landscape of oncogenic signatures across human cancers," Nat. Genet., 2013, 45(10):1127-33.
Ciriello et al., "Mutual exclusivity analysis identifies oncogenic network modules," Genome Research, 2012, 22(2):398-406.
Citro et al., "Inkblot: a neurological diagnostic decision support system integrating causal and anatomical knowledge," Artificial Intelligence in Medicine, Jul. 1997, 10(3):257-67.
Cloney, "Integrating gene variation and expression to understand complex traits," Nature Reviews Genetics, Apr. 2016, 17(4):194, 1 page.
Cooper et al., "A Bayesian algorithm for detecting CDC Category A outbreak diseases from emergency department chief complaints," Advances in Disease Surveillance, 2007, 2(2):45, 1 page.
Cooper et al., "A Bayesian method for constructing Bayesian belief networks from databases," Uncertainty Proceedings, 1991, 86-94.
Cooper et al., "A Bayesian method for the induction of probabilistic networks from dat, " Machine Learning, Oct. 1992, 9(4):309-47.
Cooper et al., "A method for detecting and characterizing outbreaks of infectious disease from clinical reports," Journal of Biomedical Informatics, Feb. 2015, 53:15-26.
Cooper et al., "An efficient bayesian method for predicting clinical outcomes from genome-wide data," AMIA Annu Symp Proc., Nov. 2010, 2010:127-31.
Cooper et al., "An evaluation of machine-learning methods for predicting pneumonia mortality," Artificial Intelligence in Medicine, Feb. 1997, 9(2):107-38.
Cooper et al., "An experiment comparing lexical and statistical methods for extracting MeSH terms from clinical free text," Journal of the American Medical Informatics Association, Jan. 1998, 5(1):62-75.
Cooper et al., "Bayesian biosurveillance of disease outbreak" arXiv preprint arXiv, Jul. 2012, 94-103.
Cooper et al., "Deriving the expected utility of a predictive model when the utilities are uncertain," AMIA Annu Symp Proc., 2005,161-5.
Cooper et al., "IPS: A System that Uses Machine Learning to Help Locate Patient Records for Clinical Research," Proceedings of the AMIA Symposium, 2001, pp. 813, 1 page.
Cooper et al., "Nestor: A Computer-Based Medical Diagnostic Aid That Integrates Causal and Probabilistic Knowledge," Stanford Univ CA Dept of Computer Science, Nov. 1984, 263 pages.
Cooper et al., "Patient simulation using seamless digital video," Proceedings of the Annual Symposium on Computer Application in Medical Care, 1993, 796-800.
Cooper et al., "Predicting dire outcomes of patients with community acquired pneumonia," Journal of Biomedical Informatics, Oct. 2005, 38(5):347-66.
Cooper et al., "The center for causal discovery of biomedical knowledge from big data," Journal of the American Medical Informatics Association, Nov. 2015, 22(6):1132-6.
Cooper et al., "Tumor-specific causal inference (TCI): A bayesian method for identifying causative genome alterations within individual tumors," BioRxiv, Jan. 2017, 17 pages.
Cooper et al., "Using computer modeling to help identify patient subgroups in clinical data repositories," Proceedings of the AMIA Symposium, 1998, 180-4.
Cooper, "A Bayesian method for learning belief networks that contain hidden variables," Journal of Intelligent Information Systems, Jan. 1995, 4(1):71-88.
Cooper, "A diagnostic method that uses causal knowledge and linear programming in the application of Bayes' formula," Computer Methods and Programs in Biomedicine, Apr. 1986, 22(2):222-37.
Cooper, "A method for using belief networks as influence diagrams," arXiv preprint arXiv: 1304.2346, Mar. 2013, 55-63.
Cooper, "A simple constraint-based algorithm for efficiently mining observational databases for causal relationships," Data Mining and Knowledge Discovery, Jun. 1997, 1(2):203-24.
Cooper, "An algorithm for computing probabilistic propositions," arXiv preprint arXiv:1304.2754, Mar. 2013, 380-5.
Cooper, "An overview of the representation and discovery of causal relationships using Bayesian networks," Computation, causation, and discovery, 1999, 1999:4-62.
Cooper, "Current research directions in the development of expert systems based on belief networks," Applied Stochastic Models and Data Analysis, Mar. 1989, 5(1):39-52.
Cooper, "Defining a workable strategy to stimulate widespread adoption of electronic health records in the United States (editorial)," Journal of the American Medical Informatics Association, 2005, 12(1):1-2.
Cooper, "Probabilistic and decision-theoretic systems in medicine," Artificial Intelligence in Medicine, Aug. 1993, 5(4):289-92.
Cooper, "The computational complexity of probabilistic inference using Bayesian belief networks," Artificial Intelligence, Mar. 1990, 42(2-3):393-405.
Coussens et al., "Inflammation and cancer," Nature, Dec. 2002, 420(6917):860-7.
Cully et al., "Beyond PTEN mutations: the PI3K pathway as an integrator of multiple inputs during tumorigenesis," Nature Reviews Cancer, Mar. 2006, 6(3):184-92.
Curtis et al., "The genomic and transcriptomic architecture of 2,000 breast tumours reveals novel subgroups," Nature, Jun. 2012, 486(7403):346-52.
Danes et al., "14-3-3ζ down-regulates p53 in mammary epithelial cells and confers luminal filling," Cancer research, Mar. 2008, 68(6):1760-7.
Dara et al., "Evaluation of preprocessing techniques for chief complaint classification," Journal of Biomedical Informatics, Aug. 2008, 41(4):613-23.

(56) References Cited

OTHER PUBLICATIONS

Dash et al., "Exact model averaging with naive Bayesian classifiers," InICML, Jul. 2002, 91-8.
Dash et al., "Model averaging for prediction with discrete Bayesian networks," Journal of Machine Learning Research, Sep. 5, 2004:1177-203.
Dawson et al., "Cancer epigenetics: from mechanism to therapy," Cell, Jul. 2012, 150(1):12-27.
Dees et al., "MuSiC: identifying mutational significance in cancer genomes," Genome Res., Jul. 2012, 22(8):1589-98.
Ding et al., "Precision oncology beyond targeted therapy: Combining omics data with machine learning matches the majority of cancer cells to effective therapeutics," Molecular Cancer Research, Feb. 2018, 16(2):269-78.
Djotsa Nono et al., "Comutational prediction of genetic drivers in cancer," eLS, Feb. 2016, 16 pages.
Extended European Search Report in European Application No. 17869807.2, dated Nov. 4, 2019, 13 pages.
Ferraro et al., "The effects of natural language processing on cross-institutional portability of influenza case detection for disease surveillance," Applied Clinical Informatics, Apr. 2017, 8(2):560-80.
Ferreira et al., "Decision path models for patient-specific modeling of patient outcomes," AMIA Annual Symposium Proceedings, 2013, 413-21.
Friedman, "Inferring Cellular Networks Using Probabilistic Graphical Models," Science, Feb. 2004, 303(5659):799-805.
Gao et al., "Integrative analysis of complex cancer genomics and clinical profiles using the cBioPortal," Science signaling, Apr. 2013, 6(269):p. 11, 20 pages.
Garraway et al., "Precision oncology: an overview," J. Clin. Oncol., May 2013, 31(15):1803-5.
Golubovskaya et al., "FAK and p53 protein interactions," Anti-Cancer Agents in Medicinal Chemistry, Sep. 2011, 11(7):617-9.
Gonzalez-Perez et al., "Functional impact bias reveals cancer drivers," Nucleic Acids Research, Nov. 2012, 40(21):e169, 10 pages.
Gopalakrishnan et al., "Bayesian rule learning for biomedical data mining," Bioinformatics, Mar. 2010, 26(5):668-75.
Gross et al., "Multi-tiered genomic analysis of head and neck cancer ties TP53 mutation to 3p loss," Nature Genetics, 2014, 46(9):939-43.
Hanahan et al., "Hallmarks of cancer: the next generation," Cell, Mar. 2011, 144(5):646-74.
Hashem et al., "Human causal discovery from observational data," Proceedings of the AMIA Annual Fall Symposium, 1996, 27-31.
Haupt et al., "Mdm2 promotes the rapid degradation of p53," Nature, May 1997, 387(6630):296-9.
Hauskrecht et al., "Conditional outlier detection for clinical alerting," AMIA Annu Symp Proc., 2010, 286-90.
Hauskrecht et al., "Data-driven identification of unusual clinical actions in the ICU," InAMIA, Nov. 2013, 1 page.
Hauskrecht et al., "Evidence-based anomaly detection in clinical domains," AMIA Annu Symp Proc., 2007, 2007:319-23.
Hauskrecht et al., "Outlier detection for patient monitoring and alerting," Journal of Biomedical Informatics, Feb. 2013, 46(1):47-55.
Hauskrecht et al., "Outlier-based detection of unusual patient-management actions: an ICU study," Journal of Biomedical Informatics, Dec. 2016, 64:211-21.
Hennings-Yeomans et al., "Improving the prediction of clinical outcomes from genomic data using multiresolution analysis," IEEE/ACM Transactions on Computational Biology and Bioinformatics, May 2012, 9(5):1442-50.
Herskovits et al., "Algorithms for Bayesian belief-network precomputation," Methods of Information in Medicine, Apr. 1991, 30(2):81-9.
Herskovits et al., "Kutató: An entropy-driven system for the construction of probabilistic expert systems from databases," Proceedings of the Conference on Uncertainty in Artificial Intelligence, 1990, 54-62.
Hill et al., "Inferring causal molecular networks: empirical assessment through a community-based effort," Nature Methods, Apr. 2016, 13(4):310-8.
Hofree et al., Network-based stratification of tumor mutations. Nat. Methods, Nov. 2013, 10(11):1108-15.
Hogan et al., "The Bayesian aerosol release detector: An algorithm for detecting and characterizing outbreaks caused by an atmospheric release of Bacillus anthracis," Statistics in Medicine, Dec. 2007, 26(29):5225-52.
Horvitz et al., "Bounded conditioning: Flexible inference for decisions under scarce resources," Proceedings of the Workshop on Uncertainty in Artificial Intelligence, 1989, 181-93.
Horvitz et al., "Reflection and action under scarce resources: Theoretical principles and empirical study," InIJCAI, Aug. 1989, 1121-7.
Hou et al., "DawnRank: discovering personalized driver genes in cancer," Genome Med., Jul. 2014, 6(7):56, 16 pages.
Jabbari et al., "Discovery of causal models that contain latent variables through Bayesian scoring of independence constraints," Joint European Conference on Machine Learning and Knowledge Discovery in Databases, Sep. 2017, 142-57.
Jabbari et al., "Instance-specific Bayesian network structure learning," Proceedings of Machine Learning Research, Sep. 2018, 72:169-80.
Jabbari et al., "Obtaining Accurate Probabilistic Causal Inference by Post-Processing Calibration," ar Xiv preprint arXiv:1712.08626, Dec. 2017, 8 pages.
Jiang et al., "A Bayesian method for evaluating and discovering disease loci associations," PloS One, Aug. 2011, 6(8):e22075, 14 pages.
Jiang et al., "A Bayesian network model for spatial event surveillance," International Journal of Approximate Reasoning, 2010, 51(2):224-39.
Jiang et al., "A Bayesian spatio-temporal method for disease outbreak detection," Journal of the American Medical Informatics Association, Jul. 2010, 17(4):462-71.
Jiang et al., "A comparative analysis of methods for predicting clinical outcomes using high-dimensional genomic datasets," Journal of the American Medical Informatics Association, Oct. 2014, 21(e2):e312-9.
Jiang et al., "A fast algorithm for learning epistatic genomic relationships," AMIA Annu Symp Proc., 2010, 341-5.
Jiang et al., "A real-time temporal Bayesian architecture for event surveillance and its application to patient-specific multiple disease outbreak detection," Data Mining and Knowledge Discovery, May 2010, 20(3):328-60.
Jiang et al., "A recursive algorithm for spatial cluster detection," AMIA Annu Symp Proc, 2007, 369-373.
Jiang et al., "Bayesian prediction of an epidemic curve," Journal of Biomedical Informatics, Feb. 2009, 42(1):90-9.
Jiang et al., "Generalized AMOC curves for evaluation and improvement of event surveillance," AMIA Annu Symp Proc., 2009, 281-85.
Jiang et al., "Modeling the temporal trend of the daily severity of an outbreak using Bayesian networks," Innovations in Bayesian Networks, 2008, 169-85.
Jin et al., "Identifying informative subsets of the Gene Ontology with information bottleneck methods," Bioinformatics, Oct. 2010, 26(19):2445-51.
Kaelin, "Synthetic lethality: a framework for the development of wiser cancer therapeutics," Genome Medicine, Dec. 2009, 1(10):99, 6 pages.
Kandoth et al., "Mutational landscape and significance across 12 major cancer types," Nature, Oct. 2013, 502(7471):333-9.
Kanehisa et al., "KEGG as a reference resource for gene and protein annotation," Nucleic Acids Research, Jan. 2016, 44(D1):D457-62.
Kayaalp et al., "Predicting ICU mortality: a comparison of stationary and nonstationary temporal models," Proceedings of the AMIA Symposium, 2000, 418-22.
Kayaalp et al., "Predicting with variables constructed from temporal sequences," Proceedings of the International Workshop on Artificial Intelligence and Statistics, 2001, 220-5.

(56) References Cited

OTHER PUBLICATIONS

Kensler et al., "Cell survival responses to environmental stresses via the Keap1-Nrf2-ARE pathway," Annu. Rev. Pharmacol. Toxicol., Feburary 2007, 47(1):89-116.
Kim et al., "Heterogeneity of expression of epithelial-mesenchymal transition markers in melanocytes and melanoma cell lines," Frontiers in Genetics, May 2013, 4:97, 8 pages.
King et al., "Development and Preliminary Evaluation of a Prototype of a Learning Electronic Medical Record System," AMIA Annu Symp Proc. 2015, 1967-75.
King et al., "Eye-tracking for clinical decision support: a method to capture automatically what physicians are viewing in the EMR," AMIA Summits on Translational Science Proceedings, 2017, 512-21.
King et al., "Leveraging Eye Tracking to Prioritize Relevant Medical Record Data: Comparative Machine Learning Study," Journal of Medical Internet Research, 2020, 22(4):e15876, 12 pages.
King et al., "Using machine learning to predict the information seeking behavior of clinicians using an electronic medical record system," AMIA Annual Symposium Proceedings, 2018, 673-82.
King et al., "Using machine learning to selectively highlight patient information," Journal of Biomedical Informatics, Dec. 2019, 100:103327, 10 pages.
Kupryjańczyk et al., "p53 gene mutations and protein accumulation in human ovarian cancer," Proceedings of the National Academy of Sciences, Jun. 1993, 90(11):4961-5.
Lawrence et al., "Discovery and saturation analysis of cancer genes across 21 tumour types, " Nature, Jan. 2014, 505(7484):495-501.
Lawrence et al., "Mutational heterogeneity in cancer and the search for new cancer-associated genes, " Nature, Jul. 2013, 499(7457):214-8.
Lengerich et al., "Learning sample-specific models with low-rank personalized regression," Advances in Neural Information Processing Systems, 2019,570-80.
Lengerich et al., "Personalized regression enables sample-specific pan-cancer analysis, " Bioinformatics, 2018, 34(13):1178-i186.
Li et al., "Constitutional and somatic rearrangement of chromosome 21 in acute lymphoblastic leukaemia," Nature, Mar. 2014, 508(7494):98-102.
Lieben, "Complex traits: Repeat, repeat, repeat—gene expression variability explained," Nat. Rev. Genet., 2016, 17(2):68-9.
Lowe et al., "Building a medical multimedia database system to integrate clinical information: an application of high-performance computing and communications technology," Bulletin of the Medical Library Association, Jan. 1995, 83(1):57-64.
Lu et al., "14-3-3ζ cooperates with ErbB2 to promote ductal carcinoma in situ progression to invasive breast cancer by inducing epithelial-mesenchymal transition," Cancer cell, Sep. 2009, 16(3):195-207.
Lu et al., "Finding pathway structures in protein interaction networks," Algorithmica, Aug. 2007, 48(4):363-74.
Lu et al., "From data towards knowledge: revealing the architecture of signaling systems by unifying knowledge mining and data mining of systematic perturbation data," PloS one, Apr. 2013, 8(4):e61134.
Lu et al., "Identifying driver genomic alterations in cancers by searching minimum-weight, mutually exclusive sets," PLoS Comput Biol., Aug. 2015, 11(8):e1004257, 20 pages.
Lu et al., "Integrating genome and functional genomics data to reveal perturbed signaling pathways in ovarian cancers," AMIA Summits on Translational Science Proceedings, 2012, 72-8.
Lu et al., "Signal-oriented pathway analyses reveal a signaling complex as a synthetic lethal target for p53 mutations," Cancer Research, Dec. 2016, 76(23):6785-94.
Lu, "From Big Data to Bedside: Filling Gaps from Genome to Peronalized Cancer Therapy," Presented at University of Texas Health Services seminar, Oct. 12, 2015, 15 pages.
Lustgarten et al., "Application of an efficient Bayesian discretization method to biomedical data," BMC Bioinformatics, Dec. 2011, 12(1):309, 15 pages.
Maher et al., "Chromothripsis and human disease: piecing together the shattering process," Cell, Jan. 2012, 148(1-2):29-32.
Mani et al., "A study in causal discovery from population-based infant birth and death records," Proceedings of the AMIA Symposium, 1999, 315-9.
Mani et al., "Causal discovery from medical textual data," Proc AMIA Symp., 2000, 542-6.
Mani et al., "Causal discovery using a Bayesian local causal discovery algorithm," Medinfo, Aug. 2004, 731-5.
Mani et al., "Defining genetic interaction," Proceedings of the National Academy of Sciences, Mar. 2008, 105(9):3461-6.
Markowetz et al., "Nested effects models for high-dimensional phenotyping screens," Bioinformatics, Jul. 2007, 23(13):i305-12.
Menon et al., "Somatic copy number alterations by whole-exome sequencing implicates YWHAZ and PTK2 in castration-resistant prostate cancer," The Journal of pathology, 2013, 231(4):505-16.
Mermel et al., "GISTIC2. 0 facilitates sensitive and confident localization of the targets of focal somatic copy-number alteration in human cancers," Genome Biology, Apr. 2011, 12(4):R41, 14 pages.
Middleton et al., "Accelerating U.S. EHR adoption: how to get there from here. recommendations based on the 2004 ACMI retreat." Journal of the American Medical Informatics Association, Jan. 2005, 12(1):13-9.
Middleton et al., "Probabilistic diagnosis using a reformulation of the internist-1/qmr knowledge base," Methods of Information in Medicine, 1991, 30(4):256-67.
Miller et al., "Chartline: providing bibliographic references relevant to patient charts using the UMLS Metathesaurus Knowledge Sources," Proceedings of the Annual Symposium on Computer Application in Medical Care, 1992, 86-90.
Millett et al., "The design and evaluation of a Bayesian system for detecting and characterizing outbreaks of influenza," Online Journal of Public Health Informatics, 2019, 11(2):e6, 19 pages.
Monti et al., "A latent variable model for multivariate discretization," Aistats, Jan. 1999, 6 pages.
Monti et al., "A multivariate discretization method for learning Bayesian networks from mixed data," Proceedings of the Fourteenth Conference on Uncertainty in Artificial Intelligence, Jul. 1998, 404-13.
Monti et al., "Bounded recursive decomposition: a search-based method for belief-network inference under limited resources," International Journal of Approximate Reasoning, Jul. 1996, 15(1):49-75.
Monti et al., "Consensus clustering: a resampling-based method for class discovery and visualization of gene expression microarray data," Machine Learning, Jul. 2003, 52(1-2):91-118.
Monti et al., "Learning Bayesian belief networks with neural network estimators," Advances in Neural Information Processing Systems, 1997, 578-84.
Monti et al., "The impact of modeling the dependencies among patient findings on classification accuracy and calibration," Proceedings of the AMIA Symposium, 1998, 592-6.
Muller et al., "Mutant p53 in cancer: new functions and therapeutic opportunities," Cancer Cell, Mar. 2014, 25(3):304-17.
Naeini et al., "An assessment of the calibration of causal relationships learned using rfci and bootstrapping," 4th Workshop on Data Mining for Medical Informatics: Causal Inference for Health Data Analytics, 2017, 7 pages.
Naeini et al., "Binary classifier calibration using a Bayesian nonparametric approach," Proceedings of the 2015 SIAM International Conference on Data Mining, Jun. 2015, 208-16.
Naeini et al., "Binary classifier calibration using an ensemble of linear trend estimation," Proceedings of the 2016 SIAM International Conference on Data Mining , Jun. 2016, 261-9.
Naeini et al., "Binary classifier calibration using an ensemble of near isotonic regression models," Proc IEEE Int Conf Data Min, Dec. 2016, 360-9.
Naeini et al., "Binary classifier calibration using an ensemble of piecewise linear regression models," Knowledge and Information Systems, Jan. 2018, 54(1):151-70.
Naeini et al., "Obtaining well calibrated probabilities using Bayesian binning," Proceedings of the Conference of the Association for the Advancement of Artificial Intelligence, 2015, 2901-7.

(56) References Cited

OTHER PUBLICATIONS

Neill et al., "A Bayesian scan statistic for spatial cluster detection," Advances in Disease Surveillance, 2006, 1:55.
Neill et al., "A multivariate Bayesian scan statistic for early event detection and characterization," Machine Learning, Jun. 2010, 79(3):261-82.
Nono et al., "Computational prediction of genetic drivers in cancer," eLS, 2016, 16 pages.
Paez et al., "EGFR mutations in lung cancer: correlation with clinical response to gefitinib therapy," Science, Jun. 2004, 304(5676):1497-500.
Parker et al., "Supervised risk predictor of breast cancer based on intrinsic subtypes," Journal of Clinical Oncology, Mar. 2009, 27(8):1160-7.
PCT International Preliminary Report on Patentability in International Appln. No. PCT/2017/061373, dated May 14, 2019, 7 pages.
PCT International Search Report and Written Opinion in International Appln. No. PCT/US2017/061373, dated Mar. 26, 2018, 10 pages.
Pe'er, "Bayesian network analysis of signaling networks: a primer," Sci. STKE, 2005, 2005(281):p. 14, 13 pages.
Pearl, "Causality: Models, Reasoning and Inference," Cambridge University Press, 2009, 675-85.
Piccart-Gebhart et al., "Trastuzumab after adjuvant chemotherapy in HER2-positive breast cancer," N. Engl. J. Med., Oct. 2005, 353(16):1659-72.
Pineda et al., "Comparison of machine learning classifiers for influenza detection from emergency department free-text reports," Journal of Biomedical Informatics, Dec. 2015, 58:60-9.
Pineda et al., "Detection of patients with influenza syndrome using machine- learning models learned from emergency department reports," Online Journal of Public Health Informatics, Mar. 2013, 5(1):e41.
Qu et al., "A patient-specific algorithm for the detection of seizure onset in long-term EEG monitoring: Possible use as a warning device," IEEE Transactions on Biomedical Engineering, 1997, 44(2):115-22.
Razi et al., "Non-linear Bayesian framework to determine the transcriptional effects of cancer-associated genomic aberrations," Conference of the IEEE Engineering in Medicine and Biology Society, Aug. 2015,6514-8.
Reva et al., "Predicting the functional impact of protein mutations: application to cancer genomics," Nucleic Acids Res., Sep. 2011, 39(17):e118, 14 pages.
Rockman et al., "Genetics of global gene expression," Nat. Rev. Genet., Nov. 2006, 7(11):862-72.
Rolka et al., "Issues in applied statistics for public health bioterrorism surveillance using multiple data streams: research needs," Statistics in Medicine, Apr. 2007, 26(8):1834-56.
Rubio-Perez et al., "In silico prescription of anticancer drugs to cohorts of 28 tumor types reveals targeting opportunities," Cancer Cell, Mar. 2015, 27(3):382-96.
Sanchez-Garcia et al., "Integration of genomic data enables selective discovery of breast cancer drivers," Cell, Dec. 2014, 159(6): 1461-75.
Schaefer et al., "Correcting for the study bias associated with protein-protein interaction measurements reveals differences between protein degree distributions from different cancer types," Front. Genet., Aug. 2015, 6:260, 8 pages.
Scheines et al., "Piecewise linear instrumental variable estimation of causal influence," Proceedings of the International Workshop on Artificial Intelligence and Statistics, 2001, 286-91.
Schulam et al., "A framework for individualizing predictions of disease trajectories by exploiting multi-resolution structure," Advances in Neural Information Processing Systems, 2015, 748-56.
Schulam et al., "Integrative analysis using coupled latent variable models for individualizing prognoses," Journal of Machine Learning Research, 2016, 17(1):8244-78.
Segal and Kim, "The modular era of functional genomics, " Genome Biol., Apr. 2003, 4(5):317, 2 pages.

Segal et al., "A module map showing conditional activity of expression modules in cancer," Nature Genetics, 2004, 36(10):1090-8.
Seymour et al., "Derivation, validation, and potential treatment implications of novel clinical phenotypes for sepsis," Jama, May 2019, 321(20):2003-17.
Sheiner et al., "Forecasting individual pharmacokinetics," Clinical Pharmacology & Therapeutics, 1979, 26(3):294-305.
Shen et al., "A Bayesian biosurveillance method that models unknown outbreak diseases," NSF Workshop on Intelligence and Security Informatics, May 2007, 209-15.
Shen et al., "A generalization of the AMOC curve," Advances in Disease Surveillance, 2006, 1(1):65.
Shen et al., "A new prior for Bayesian anomaly detection," Methods of Information in Medicine, 2010, 49(1):44-53.
Shen et al., "An Outbreak Detection Algorithm that Efficiently Performs Complete Bayesian Model Averaging Over All Possible Spatial Distributions of Disease," Adv Dis Surveill., 2007, 4:113.
Shen et al., "Bayesian modeling of unknown diseases for biosurveillance," AMIA Annu Symp Proc., 2009, 589-93.
Shen et al., "Estimating the expected warning time of outbreak-detection algorithms," Advances in Disease Surveillance, 2005, 1 page.
Shen et al., "Estimating the joint disease outbreak-detection time when an automated biosurveillance system is augmenting traditional clinical case finding," Journal of Biomedical Informatics, Apr. 2008, 41(2):224-31.
Shen et al., "Multivariate Bayesian modeling of known and unknown causes of events—An application to biosurveillance," Computer Methods and Programs in Biomedicine, Sep. 2012, 107(3):436-46.
Shiffman et al., "Building a speech interface to a medical diagnostic system," IEEE Expert, Feb. 1991, 6(1):41-50.
Shwe et al., "A probabilistic reformulation of the Quick Medical Reference System," Proceedings of the Annual Symposium on Computer Application in Medical Care, Nov. 1990, 790-4.
Shwe et al., "An empirical analysis of likelihood-weighting simulation on a large, multiply connected medical belief network," Computers and Biomedical Research, Oct. 1991, 24(5):453-75.
Shwe et al., "An empirical analysis of likelihood-weighting simulation on a large, multiply-connected belief network," arXiv preprint arXiv: 1304.1141, Mar. 2013, 498-508.
Shwe et al., "Probabilistic diagnosis using a reformulation of the Internist-1/QMR knowledge base," Methods of Information in Medicine, 1991, 30(4):241-55.
Spirtes et al., "An experiment in causal discovery using a pneumona database," Aistats, 1999, 7 pages.
Stransky et al., "The landscape of kinase fusions in cancer," Nat. Commun., Sep. 2014, 5(1):4846, 10 pages.
Suermondt and Cooper, "An evaluation of explanations of probabilistic inference," Computers and Biomedical Research, Jun. 1993, 26(3):242-54.
Suermondt et al., "A combination of exact algorithms for inference on Bayesian belief networks," International Journal of Approximate Reasoning, Nov. 1991, 5(6):521-42.
Suermondt et al., "An evaluation of explanations of probabilistic inference," Proc Annu Symp Comput Appl Med Care, 1992,579-85.
Suermondt et al., "Initialization for the method of conditioning in Bayesian belief networks," Artificial Intelligence, Jun. 1991, 50(1):83-94.
Suermondt et al., "Probabilistic inference in multiply connected belief networks using loop cutsets," International Journal of Approximate Reasoning, Jul. 1990, 4(4):283-306.
Šutovský et al., "Hierarchical explanation of inference in Bayesian networks that represent a population of independent agents," 18th European Conference on Artificial Intelligence, Jul. 2008, 214-8.
Sverchkov et al., "A Bayesian Approach for Identifying Multivariate Differences Between Groups," Adv Intell Data Anal., 2015, 9385:275-285.
Sverchkov et al., "A multivariate probabilistic method for comparing two clinical datasets," Proceedings of the 2nd ACM SIGHIT International Health Informatics Symposium, Jan. 2012, 795-800.

(56) References Cited

OTHER PUBLICATIONS

Sverchkov et al., "Spatial cluster detection using dynamic programming," BMC Medical Informatics and Decision Making, Dec. 2012, 12(1):22, 21 pages.
Tamborero et al., "Comprehensive identification of mutational cancer driver genes across 12 tumor types," Scientific Reports, Oct. 2013, 3:2650.
Tamborero et al., "Oncodrive-CIS: a method to reveal likely driver genes based on the impact of their copy No. changes on expression," PLoS One, 2013, 8(2):e55489, 9 pages.
Thomas-Chollier et al., "Transcription factor binding predictions using TRAP for the analysis of ChIP-seq data and regulatory SNPs," Nat. Protoc., 2011, 6(2):1860-9.
Thorpe et al., "PI3K in cancer: divergent roles of isoforms, modes of activation and therapeutic targeting," Nat. Rev. Cancer, 2015, 15(1):7-24.
Tseng et al., "PVT1 dependence in cancer with MYC copy-number increase," Nature, Jun. 2014, 512(7512):82-6.
Tsui et al., "Automated influenza case detection for public health surveillance and clinical diagnosis using dynamic influenza prevalence method," Journal of Public Health, Dec. 2018, 40(4):878-85.
Tsui et al., "Probabilistic case detection for disease surveillance using data in electronic medical records," Online Journal of Public Health Informatics, 2011, 3(3): 17 pages.
Valko et al., "Conditional anomaly detection methods for patient-management alert systems," International Conference on Machine Learning, 2008, 2008: 15 pages.
Valko et al., "Conditional anomaly detection with soft harmonic functions," 2011 IEEE 11th International Conference on Data Mining, Dec. 2011, 735-43.
Vandin et al., "De novo discovery of mutated driver pathways in cancer," Genome Res., Feb. 2012, 22(2):375-85.
Venet et al., "Most random gene expression signatures are significantly associated with breast cancer outcome," PLoS Comput Biol., Oct. 2011, 7(10):e1002240, 8 pages.
Verdu and Rosenberg, "A general mechanistic model for admixture histories of hybrid populations," Genetics, Dec. 2011, 189(4):1413-26.
Villamarín et al., "A method for estimating from thermometer sales the incidence of diseases that are symptomatically similar to influenza," Journal of Biomedical Informatics, Jun. 2013, 46(3):444-57.
Visweswaran et al., "Detecting adverse drug events in discharge summaries using variations on the simple Bayes model," AMIA Annual Symposium Proceedings, 2003, 689-93.
Visweswaran et al., "Identifying Deviations from Usual Medical Care using a Statistical Approach," AMIA Annu Symp Proc., Nov. 2010, 827-31.
Visweswaran et al., "Instance-specific Bayesian model averaging for classification," Advances in Neural Information Processing Systems, 2005, 1449-56.
Visweswaran et al., "Learning Instance-Specific Predictive Models," Journal of Machine Learning Research, Dec. 2010, 11:3333-69.
Visweswaran et al., "Learning patient-specific predictive models from clinical data," J. Biomed. Inform., Oct. 2010, 43(5):669-85.
Visweswaran et al., "Patient-specific models for predicting the outcomes of patients with community acquired pneumonia," AMIA Annu. Symp. Proc., 2005, 2005:759- 63.
Visweswaran et al., "Personalized modeling for prediction with decision-path models," PLoS One, Jun. 2015, 10(6):e0131022, 15 pages.
Visweswaran et al., "Risk Stratification and Prognosis Using Predictive Modelling and Big Data Approaches," Personalized and Precision Medicine Informatics, 2020, 87-105.
Vogelstein et al., "Cancer genome landscapes," Science, Mar. 2013, 339(6127):1546-58.
Wadhwa et al., "Analysis of a failed clinical decision support system for management of congestive heart failure," AMIA Annu Symp Proc., 2008, 2008:773-7.
Wagner et al., "A Decision-Theoretic Model of Disease Surveillance and Control and a Prototype Implementation for the Disease Influenza," 2012 IEEE 28th International Conference on Data Engineering Workshops, 2012, 49-54.
Wagner et al., "Decision-theoretic information pretrieval: a generalization of reminding," Proceedings of the Annual Symposium on Computer Application in Medical Care, 1993, 512-6.
Wagner et al., "Evaluation of a belief-network-based reminder system that learns from utility feedback," Proceedings of the Annual Symposium on Computer Application in Medical Care, 1995, 666-72.
Wagner et al., "Evaluation of a Meta-1-based automatic indexing method for medical documents," Computers and Biomedical Research, Aug. 1992, 25(4):336-50.
Wagner et al., "Probabilistic, decision-theoretic disease surveillance and control," Online Journal of Public Health Informatics, 2011, 3(3):16.
Wagner et al., "Representing Care rules in a decision-theoretic formalism," Proceedings of the AMIA Annual Fall Symposium, 1996, 582-86.
Wang et al., "Bayesian method for biological pathway discovery from high- throughput experimental data," Proceedings. 2004 IEEE Computational Systems Bioinformatics Conference, 2004, 645-6.
Webster et al., "Changes in tropical cyclone No. duration, and intensity in a warming environment," Science, Sep. 2005, 309(5742):1844-6.
Wei et al., "A global map of p53 transcription-factor binding sites in the human genome," Cell, Jan. 2006, 124(1):207-19.
Wei et al., "The application of naive Bayes model averaging to predict Alzheimer's disease from genome-wide data," Journal of the American Medical Informatics Association, Jul. 2011, 18(4):370-5.
Weinberg, "pRb and Control of the Cell Cycle Clock" The Biology of Cancer, 36 pages.
Wong et al., "Bayesian biosurveillance using multiple data streams," Morbidity and Mortality Weekly Report (Supplement), 2005, 54:63-9.
Wong et al., "Bayesian network anomaly pattern detection for disease outbreaks," Proceedings of the 20th International Conference on Machine Learning (ICML-03), 2003, 808-15.
Wong et al., "Revealing targeted therapy for human cancer by gene module maps," Cancer Res., Jan. 2008, 68(2):369-78.
Wong et al., "Rule-based anomaly pattern detection for detecting disease outbreaks," AAAI/IAAI, Jul. 2002, 217-23.
Wong et al., "What's strange about recent events (WSARE): an algorithm for the early detection of disease outbreaks," Journal of Machine Learning Research, 2005, 6:1961-98.
Wong et al., "WSARE: what's strange about recent events?," Journal of Urban Health, Mar. 2003, 80(1):166-75.
Wu et al., "MiR-1207 overexpression promotes cancer stem cell-like traits in ovarian cancer by activating the Wnt/beta-catenin signaling pathway," Oct. 2015, Oncotarget, 6(30):28882-94.
Xue et al., "Tumour-specific Causal Inference Discovers Distinct Disease Mechanisms Underlying Cancer Subtypes," Scientific Reports, Sep. 2019, 9(1):1-3.
Ye et al., "A study of the transferability of influenza case detection systems between two large healthcare systems," PloS One, Apr. 2017, 12(4):e0174970, 23 pages.
Yoo and Cooper, "A computer-based microarray experiment design-system for gene-regulation pathway discovery," AMIA Annual Symposium Proceedings, 2003, 2003:733, 5 pages.
Yoo and Cooper, "An evaluation of a system that recommends microarray experiments to perform to discover gene-regulation pathways," Artificial Intelligence in Medicine, Jun. 2004, 31(2):169-82.
Yoo and Cooper, "Discovery of causal relationships in a gene-regulation pathway from a mixture of experimental and observational DNA microarray data," Biocomputing, 2002, 498-509.
Yoo and Cooper, "Discovery of gene-regulation pathways using local causal search," Proceedings of the AMIA Symposium, 2002, 914-8.

(56) References Cited

OTHER PUBLICATIONS

Yoo et al., "A control study to evaluate a computer-based microarray experiment design recommendation system for gene-regulation pathways discovery," Journal of Biomedical Informatics, Apr. 2006, 39(2):126-46.
Zack et al., "Pan-cancer patterns of somatic copy No. alteration," Nat. Genet., Sep. 2013, 45(10):1134-40.
Zheng et al., "Lazy learning of Bayesian rules, " Machine Learning, 2000, 41(1):53-84.
Zheng et al., "Spliced MDM2 isoforms promote mutant p53 accumulation and gain-of-function in tumorigenesis," Nat. Commun., Dec. 2013, 4(1):2996, 26 pages.
Zheng et al., "Spliced MDM2 isoforms promote mutant p53 accumulation and gain-of-function in tumorigenesis," Nature communications, Dec. 2013, 4(1):1-2.
Andrews et al., "Scoring Bayesian networks of mixed variables," International Journal of Data Science and Analytics, 2018, 6(1):3-18.
Mezger et al., "A statistical approach for detecting deviations from usual medical care," Abstract, Presented at Proceedings of the AMIA Annual Symposium Proceedings, Chicago, IL, USA, Nov. 10-14, 2007; AMIA Annu. Symp. Proceedings, Oct. 2007, 1051, 2 pages.

\* cited by examiner

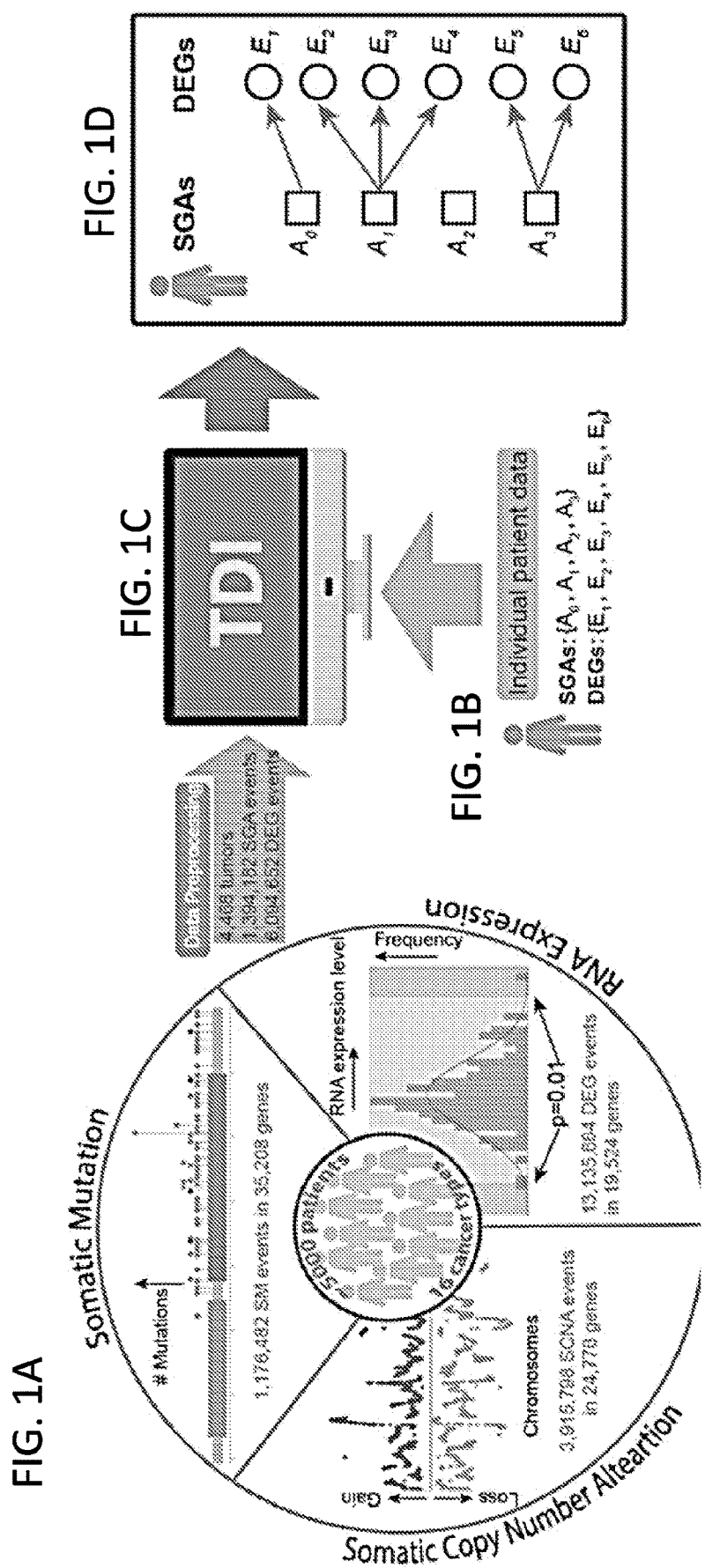

SM ● CN amplification ● CN deletion

FIG. 3A
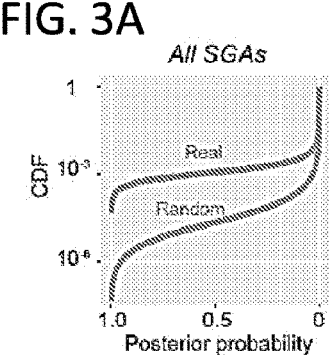
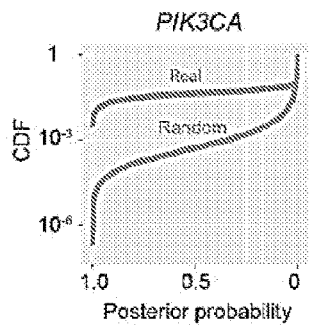
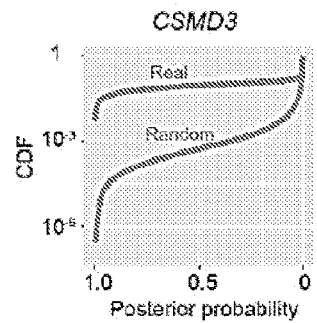
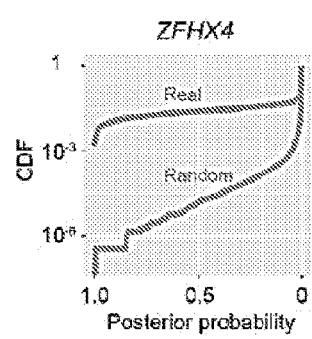
FIG. 3B
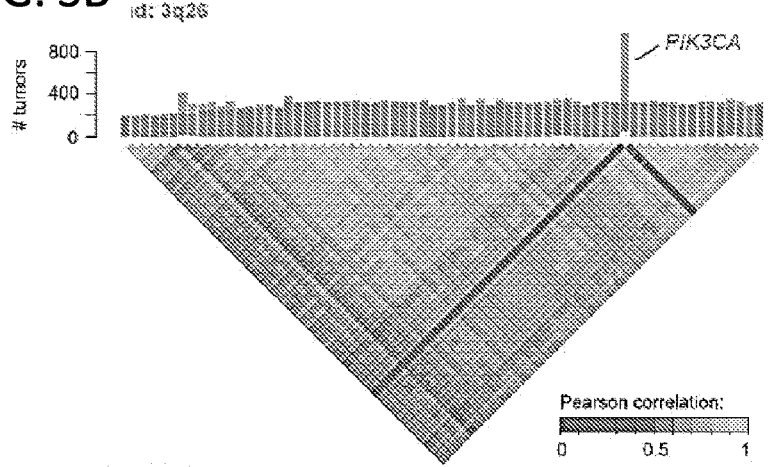
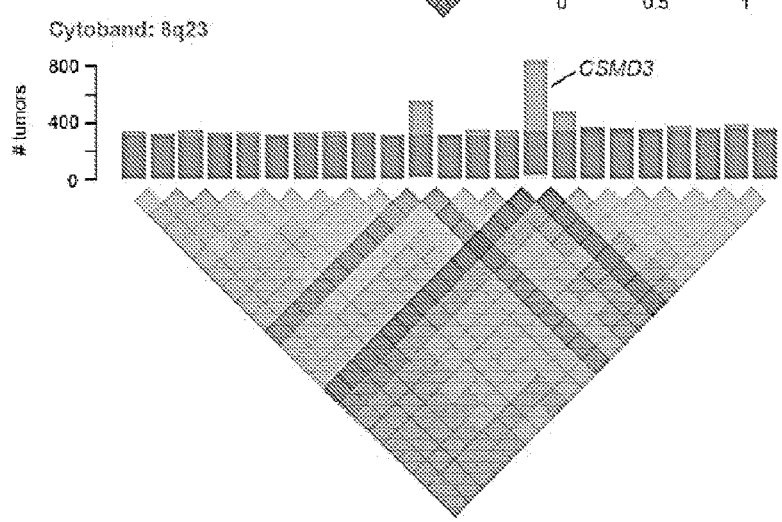
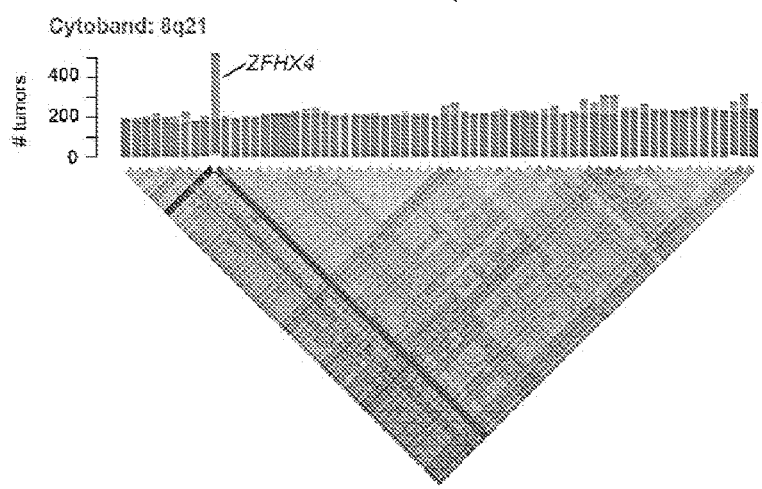

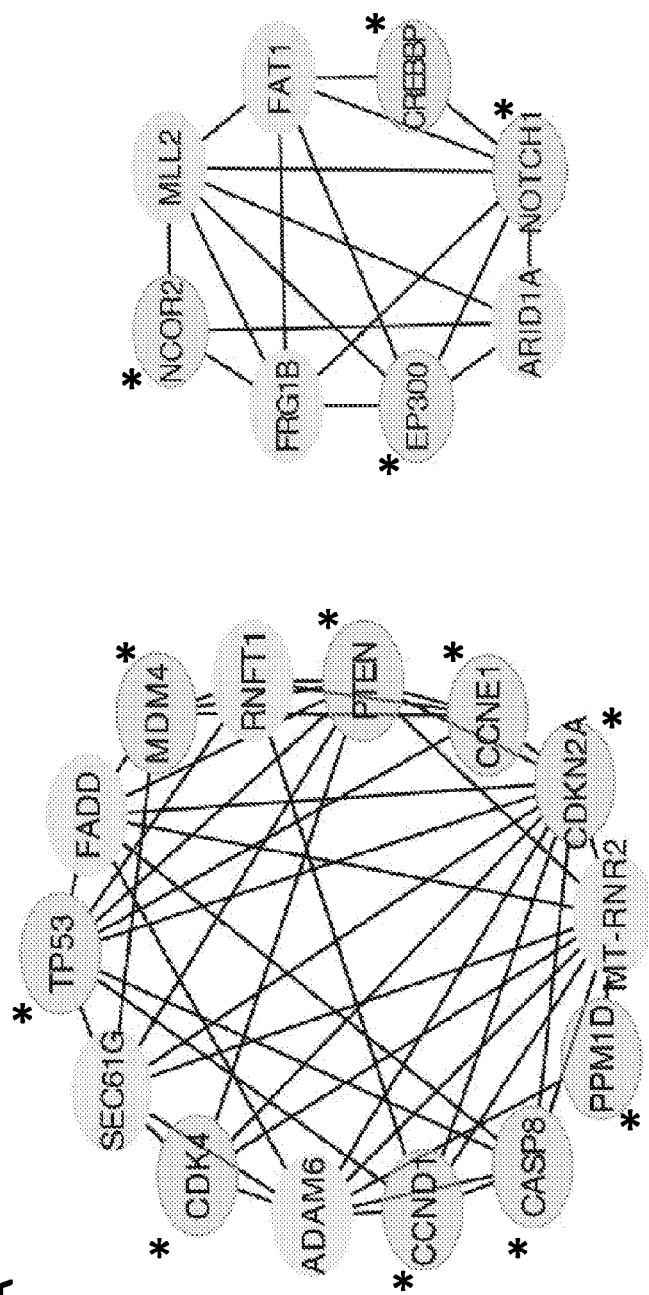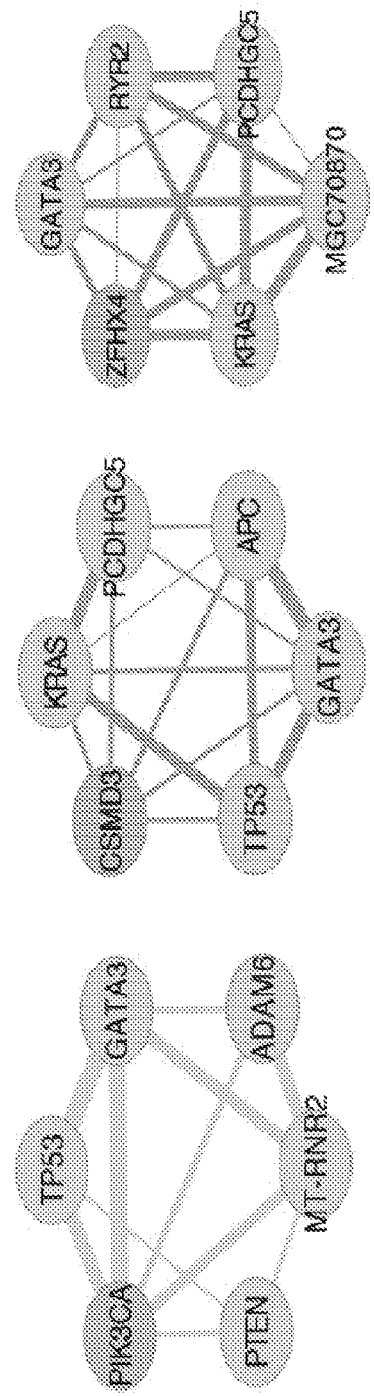
FIG. 5A
FIG. 5B

SEQUENCE LISTING

<160> NUMBER OF SEQ ID NOS: 4

<210> SEQ ID NO 1
<211> LENGTH: 25
<212> TYPE: DNA
<213> ORGANISM: artificial sequence
<220> FEATURE:
<223> OTHER INFORMATION: Oligonucleotide priimer

<400> SEQUENCE: 1
gguauauuac gaagaauugc agagt          25

<210> SEQ ID NO 2
<211> LENGTH: 25
<212> TYPE: DNA
<213> ORGANISM: artificial sequence
<220> FEATURE:
<223> OTHER INFORMATION: Oligonucleotide primer

<400> SEQUENCE: 2
acaaauggag gaauacuaac aacag          25

```
<210> SEQ ID NO 3
<211> LENGTH: 25
<212> TYPE: DNA
<213> ORGANISM: artificial sequence
<220> FEATURE:
<223> OTHER INFORMATION: Oligonucleotide primer

<400> SEQUENCE: 3
cgaugcuuca gaaacaaagg aagac                                        25

<210> SEQ ID NO 4
<211> LENGTH: 25
<212> TYPE: DNA
<213> ORGANISM: artificial sequence
<220> FEATURE:
<223> OTHER INFORMATION: oligonucleotide primer

<400> SEQUENCE: 4
ggaacgacag agaaauaaag auuca                                        25
```

IDENTIFICATION OF INSTANCE-SPECIFIC SOMATIC GENOME ALTERATIONS WITH FUNCTIONAL IMPACT

CROSS-REFERENCE TO RELATED APPLICATIONS

This application is a National Stage application under 35 U.S.C. § 371 of International Application No. PCT/US2017/061373, having an International Filing Date of Nov. 13, 2017, which claims the benefit of U.S. Provisional Application No. 62/420,936, filed Nov. 11, 2016. The disclosures of the prior applications are considered part of (and are incorporated by reference in) the disclosure of this application.

ACKNOWLEDGMENT OF GOVERNMENT SUPPORT

This invention was made with government support under Grant Nos. LM010144, HG008540, and HG007934 awarded by the National Institutes of Health. The government has certain rights in the invention.

FIELD

The present disclosure relates to methods and processes for the characterization of cancer and more particularly to methods for identifying somatic genome alterations with functional impact in the genome of a tumor.

BACKGROUND

Cancer is a highly complex disease caused by a variety of somatic genome alterations (SGAs), including, but not limited to, mutations, DNA copy number variations, gene fusions, chromosome rearrangement, and epigenetic changes. A tumor commonly hosts a unique combination of SGAs ranging in number from hundreds to thousands, of which only a small fraction contribute to tumorigenesis (drivers or SGAs with functional impact, SGA-FIs), while the rest are non-consequential with respect to cancer (passengers). A key task of precision oncology is to identify and target cellular aberrations resulting from driver SGAs in an individual tumor.

Current methods for identifying candidate driver genes concentrate on finding those that have a higher than expected mutation rate in a cohort of tumor samples. Mutation-frequency-oriented models have successfully identified many major oncogenes and tumor suppressors across cancer types. However, these methods are constrained by the need to define the baseline mutation rate, and as such, different models lead to different findings. Furthermore, current approaches are limited in their ability to determine whether a gene altered at a low frequency (prevalence<2%) is a driver.

SUMMARY

Described herein are novel methods for identifying SGA-FIs in a tumor. Unlike prior methods that focus on identification SGA-FIs at a cohort level, the disclosed methods can identify tumor-specific SGA-FIs. Accordingly, such methods are referred to herein as Tumor-specific Driver Identification (TDI) methods.

In some embodiments, a computer-implemented method for identifying a SGA-FI in a genome of a tumor t is provided. The method comprises receiving a set of SGAs in the genome of t, and receiving a set of differentially expressed genes (DEGs) in the genome of t. A bipartite causal Bayesian network (CBN) with maximal posterior probability is generated from these sets of data, wherein the CBN with maximal posterior probability comprises causal edges pointing from SGAs in the set of SGAs to DEGs in the set of DEGs with a single causal edge pointing to each DEG. A SGA from which five or more causal edges in the CBN point to DEGs is identified as the SGA-FI in the genome of the tumor t. In several embodiments, the SGA-FI is a driver SGA.

In some embodiments, generating the CBN with maximal posterior probability comprises generating a plurality of test CBNs for the set of SGAs and the set of DEGs. A posterior probability for each test CBN in the plurality is determined, and the test CBN with the maximal posterior probability is identified as the CBN with maximal posterior probability. New approaches for determining the posterior probability for the test CBNs in the plurality are provided and include novel marginal likelihood and prior probability calculations.

In additional embodiments, computer-implemented methods, computer systems, and computer readable media are provided.

The foregoing and other features and advantages of the disclosed technology will become more apparent from the following detailed description, which proceeds with reference to the accompanying figures.

BRIEF DESCRIPTION OF THE FIGURES

FIGS. 1A-1D illustrate the steps of an embodiment of the TDI method. 1A. A compendium of cancer omics data is used as the training dataset. Three types of data from the pan-cancer tumors were used in this study, including somatic mutation (SM) data (1,176,482 mutation events in 35,208 genes), somatic copy number alteration (SCNA) data (3,915,798 alteration events in 24,776 genes), and gene expression data (13,135,684 DEG events in 19,524 genes). SM and SCNA data were integrated as SGA data. Expression of each gene in each tumor was compared to a distribution of the same gene in the "normal control" samples, and, if a gene's expression value was outside the significance boundary, it was designated as a DEG in the tumor. The final dataset included 4,468 tumors with 1,394,182 SGA events and 6,094,652 DEG events. 1B. A set of SGAs and a set of DEGs from an individual tumor as input for the TDI method. 1C. The TDI method infers the causal relationships between SGAs and DEGs for a given tumor t and outputs a tumor-specific causal model. 1D. A hypothetic model illustrates the results of analysis using the TDI method. In this tumor, $SGA\_SET_t$ has three SGAs plus the non-specific factor $A_0$, and $DEG\_SET_t$ has six DEG variables. Each $E_i$ must have exactly one arc into it, which represents having one cause among the variables in $SGA\_SET_t$. In this model, $E_1$ is caused by $A_0$; $E_2$, $E_3$, $E_4$ are caused by $A_1$; $E_5$, $E_6$ are caused by $A_3$; $A_2$ does not have any regulatory impact.

FIGS. 3A and 3B illustrate the statistical characteristics of the TDI method. 3A. The causal relationships inferred by the TDI method are statistically sound. Plots in this panel show the cumulative distribution of the posterior probabilities assigned to candidate edges when the TDI method was applied to real data and the random data, in which DEGs were randomly permutated across tumors. The top plot shows the results for the posterior probabilities for all candidate edges in the whole dataset; the rest of the plots show the posterior probabilities of the candidate edges pointing from 3 specific SGAs to all DEGs, namely, PIK3CA, CSMD3, and ZFHX4. 3B. Combining SM and SCNA data creates a "linkage disequilibrium" among genes that are enclosed in a common SCNA fragments. The chromosome cytobands enclosing three example genes (PIK3CA, CSMD3, and ZFHX4) are shown. The bar charts show the frequency of SCNA (dark grey, standing for amplification) and SM (light grey). The disequilibrium plots beneath the bar charts depict the correlations among genes within a cytoband.

FIGS. 5A-5B illustrate that detection of functional impacts of SGA-FIs reveals functional connections among SGA-FIs. 5A. Mapping novel SGA-FIs to known pathways. Known members of the p53 and Notch1 pathways from the KEGG database that were identified as SGA-FIs using the TDI method are shown as nodes (marked with an "*") in the respective networks. An edge between a pair of nodes indicates that two SGA-FIs share significantly overlapping target DEGs. Novel SGA-FIs that were densely connected to the known members (>50% of known members) are shown as nodes. 5B. Top 5 SGA-FIs that share the most significant overlapping target DEGs with 3 SGA-FIs (PIK3CA, CSMD3, ZFHX4). An edge between a pair of SGA-FIs indicates that they share significantly overlapping target DEG sets, and the thickness of the line is proportional to the negative log of the hypergeometric p-values of overlapping target DEG sets.

SEQUENCES

Figure 2A:
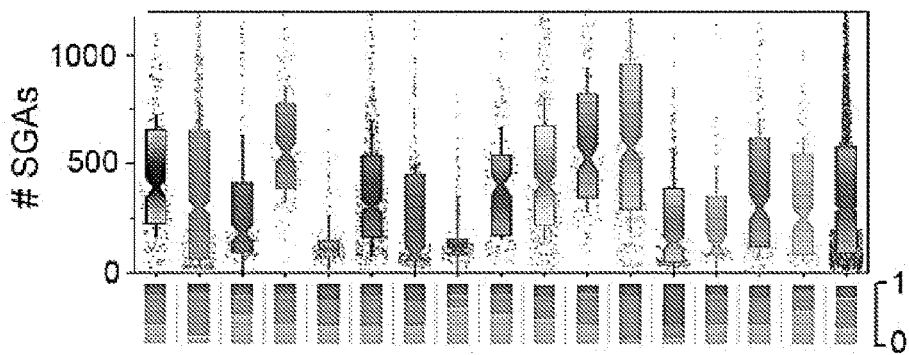
FIGS. 2A-2E illustrate the landscape of SGAs and SGA-FIs. 2A & 2B. The distributions of the number of SGAs per tumor and SGA-FIs per tumor of different cancer types. Beneath the bar box plots, the distributions of different types of SGAs (SM, copy number amplification, and deletion) are shown. 2C. Identification of SGA-FIs is independent of the alteration frequency or gene length. Darker dots indicate SGA-FIs, and lighter dots represent SGAs that were not designated as SGA-FIs. A few commonly altered genes are indicated by their gene names, where genes labeled with black font are well-known drivers, and those labeled with gray font are novel candidate drivers. 2D. A Circos plot shows SGA events and SGA-FI calls along the chromosomes. Different types of SGA events (SM, copy number amplification, deletion) are shown in the tracks 2, 3, and 4, respectively. Track 1 shows the frequency of an SGA being called as an SGA-FI. The gene names denote the top 62 SGA-FIs (some are SGA units) that were called in over 300 tumors with a call rate>0.8. Genes labeled with black font are known drivers from two TCGA reports, and gray ones are novel candidate drivers identified using the TDI method. 2E. SGA-FIs that were called in less than 300 tumors and with a call rate>0.8 are shown in this frequency-vs-call rate plot. Similarly, genes labeled with black font are known drivers from TCGA studies, and gray ones are novel candidate drivers identified using the TDI method.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~4 kb), which was created on Nov. 8, 2017 which is incorporated by reference herein.

DETAILED DESCRIPTION

I. Introduction

Identifying causative or "driver" SGAs driving the development of an individual tumor can provide insight into disease mechanisms and enable personalized modeling for cancer precision medicine. Although methods exist for identifying driver SGAs at the cohort level, few focus on the drivers of individual tumors. This disclosure provides TDI methods and related systems that infer causal relationships between SGAs and molecular phenotypes (e.g., transcriptomic, proteomic, or metabolomics changes) within a specific tumor using a CBN, in which causal edges are only allowed to point from SGAs to DEGs.

The TDI method combines the strengths of both frequency- and functional-impact oriented approaches for identifying driver SGAs in a tumor. TDI uses the frequency with which a gene g is perturbed by SGA events in a reference set of tumor genomes, D, to estimate the prior probability $P(g)$ that g is a cancer driver in any given tumor. To further incorporate information from a function-impact perspective, TDI employs the likelihood function $P(data|g)$, which represents the probability of the molecular phenotype data that is observed (e.g., DEGs) given that g is assumed to be a driver. From such priors and likelihoods, TDI derives the posterior probabilities of drivers for a given tumor. By inferring causal relationships between SGA events and molecular phenotypes, TDI can identify cancer drivers and provide insight into the disease mechanism of individual tumors.

The advantageous tumor-specific nature of the TDI method is reflected in several ways, including (notation described in more detail in Example 1):

Each tumor has a unique set of SGAs and DEGs, and TDI infers causal relationships between those two sets; thus, the resulting CBN model M is necessarily tumor specific;

The prior probability of a model $P(M)$, which is based on the component priors $P(A_j \rightarrow E_i|K)$, is tumor-specific;

Calculation of the marginal likelihood of a causal edge $P(data_i|A_j \rightarrow E_i, K)$ includes both tumor-specific and global components. The tumor-specific component is computed using SGA and DEG data from the tumors in which $A_j=1$ (i.e., "tumors like me") to evaluate how strongly $A_j$ affects $E_i$ in these tumors. The global component uses data from tumors with $A_j=0$ to calculate as $P(data_i|A_* \rightarrow E_i, K)$, where $A_*$ is an SGA that best explains the $E_i$ at the population (global) level. Thus, the TDI method provides a relative strength assessment for how strongly $A_j$ regulates $E_i$ in tumors with $A_j=1$ (tumors like the one under consideration), given the causes of $E_i$ in rest of tumor are explained by a global cause A.

The posterior probability for candidate causal edge $A_j \rightarrow E_i$ is dependent on how well other candidate causal edges explain $E_i$. As such, the posterior probability of a given edge $A_j \rightarrow E_i$ is specific to a given tumor, and the same candidate edge $A_j \rightarrow E_i$ may have different posterior probabilities in different tumors depending on the composition of the SGAs in the tumor.

As discussed in Example 1, the causal relationships inferred by the TDI method are statistically robust, validated by experimental evidence, and more sensitive and specific than prior methods of identifying driver mutations in a given tumor genome. Taken together, the novel features and advantages of the TDI method and related systems allow for surprisingly effective elucidation of driver SGAs in a tumor.

II. Abbreviations

CBN Bipartite Causal Bayesian Network
DEG Differentially Expressed Gene
SCNA Somatic Copy Number Alteration
SGA Somatic Genome Alteration
SGA-FI Somatic Genome Alteration with Functional Impact
SM Somatic Mutation
TCGA The Cancer Genome Atlas
TDI Tumor-specific Driver Identification

III. Terms and Discussion

For purposes of this description, certain aspects, advantages, and novel features of the embodiments of this disclosure are described herein. The disclosed methods and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the specification and attached figures may not show all the various ways in which the disclosed methods can be used in conjunction with other methods.

The singular terms "a", "an", and "the" include plural referents unless context clearly indicates otherwise. The term "comprises" means "includes without limitation." The term "and/or" means any one or more of the elements listed. Thus, the term "A and/or B" means "A", "B" or "A and B."

Unless otherwise noted, technical terms are used according to conventional usage. To facilitate review of the various embodiments, the following explanations of terms are provided:

Cancer: A biological condition in which a malignant tumor or other neoplasm has undergone characteristic anaplasia with loss of differentiation, increased rate of growth, invasion of surrounding tissue, and which is capable of metastasis. A neoplasm is a new and abnormal growth, particularly a new growth of tissue or cells in which the growth is uncontrolled and progressive. A tumor is an example of a neoplasm. Non-limiting examples of types of cancer include lung cancer, stomach cancer, colon cancer, breast cancer, uterine cancer, bladder cancer, head and neck cancer, kidney cancer, liver cancer, ovarian cancer, pancreas cancer, prostate cancer, and rectal cancer.

Control: A sample or standard used for comparison with an experimental sample. In some embodiments, the control is a sample obtained from a healthy individual (such as an individual without cancer) or a non-tumor tissue sample obtained from a patient diagnosed with cancer. In some embodiments, the control is a historical control or standard reference value or range of values (such as a previously tested control sample, such as a group of cancer patients with poor prognosis, or group of samples that represent baseline or normal values, such as the level of gene expression in a tumor sample).

Differentially expressed gene (DEG): A gene with an alteration (such an increase or decrease) in expression of the corresponding gene product (for example, miRNA, non-coding RNA, RNA encoding a protein, or the corresponding protein) that is detectable in a biological sample relative to a control. An "alteration" in expression includes an increase in expression (up-regulation) or a decrease in expression (down-regulation) relative to a control.

Molecular phenotypes of a tumor: A set of molecular measurements that reflect the state of cellular system of a tumor. Molecular phenotypic variations include but not limited to: DEGs, proteomic changes (quantity and chemical modification of proteins), and metabolimics changes (quantity and modification of metabolites).

Epigenetic status of a gene: Any structural feature at the molecular level of a nucleic acid (e.g., DNA or RNA) other than the primary nucleotide sequence. For instance, the epigenetic state of a genomic DNA may include its secondary or tertiary structure determined or influenced by, for example, its methylation pattern or its association with cellular proteins, such as histones, and the modifications of such proteins, such as acetylation, deacetylation, and methylation.

Gene: A segment of chromosomal DNA that contains the coding sequence for a protein, wherein the segment may include promoters, exons, introns, and other untranslated regions that control expression.

Somatic Copy Number Alteration (SCNA) of a gene: An alteration in the number of copies of a DNA in a genome including all or a portion of one or more genes. This includes homozygous deletion, single copy deletion, diploid normal copy, low copy number amplification, and high copy number amplification. In some embodiments, only genes with homozygous deletion or high copy number amplification are included in the analytical methods provided herein. SCNA can be detected with various types of tests, including, but not limited to, full genome sequencing. Somatic mutation of a gene: Any change of a chromosomal nucleic acid sequence encoding a gene or including regulatory elements of the gene. For example, mutations can occur within an exon of a gene, or changes in or near regulatory regions of genes. Types of mutations include, but are not limited to, base substitution point mutations (which are either transitions or transversions), deletions, and insertions. Missense mutations are those that introduce a different amino acid into the sequence of the encoded protein; nonsense mutations are those that introduce a new stop codon; and silent mutations are those that introduce the same amino acid often with a base change in the third position of the codon. In the case of insertions or deletions, mutations can be in-frame (not changing the frame of the overall sequence) or frame shift mutations, which may result in the misreading of a large number of codons (and often leads to abnormal termination of the encoded product due to the presence of a stop codon in the alternative frame). Synonymous somatic mutations are those that do not change amino acids in the sequence of the encoded protein and are generally biologically silent. Non-synonymous somatic mutations are those that change at least one amino acid in the sequence of the encoded protein, and therefore may alter the structure and/or function of the encoded protein. Gene mutations can be detected with various types of assays, including, but not limited to, full genome sequencing.

Somatic genome alteration (SGA): An alteration to chromosomal DNA acquired by a cell that can be passed to the progeny of the cell in the course of cell division. Non-limiting examples of SGAs include somatic mutation (SM) of a gene in chromosomal DNA, somatic copy number alteration (SCNA) of a gene in chromosomal DNA, somatic single nucleotide variations in chromosomal DNA that alter regulation of protein-coding genes, and alterations in the epigenetic status of a gene in chromosomal DNA.

Somatic genome alteration with functional impact (SGA-FI): A SGA that leads to or causes a change in a molecular phenotype of a cell, such as differential gene expression.

Driver SGA: An SGA-FI that leads to or causes malignancy of a cell. In some embodiments, a SGA-FI that leads to or causes differential expression of at least five different genes is identified as a driver SGA. More generally, a driver SGA is a genomic event that occurs in cancer cells and bears biological impact on molecular phenotypes that contribute to cancer development in a subject.

Subject: A living multi-cellular vertebrate organism, a category that includes human and non-human mammals Tumor: An abnormal growth of cells, which can be benign or malignant. Cancer is a malignant tumor, which is characterized by abnormal or uncontrolled cell growth.

Features often associated with malignancy include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc.

The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant."

Examples of hematological tumors include leukemias, including acute leukemias (such as 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyrgioma, ependymoma, pinealoma, hemangioblastoma, acoustic neuroma, oligodendroglioma, meningioma, melanoma, neuroblastoma and retinoblastoma). In several examples, a tumor is melanoma, lung cancer, lymphoma, breast cancer or colon cancer.

The disclosed methods can be used to identify SGA-FIs in tumors, such as any of the types of tumors listed above.

Tumor genome: The full complement of chromosomal DNA found within cells from a tumor.

IV. Methods of Identifying a SGA-FI

Figure 11:
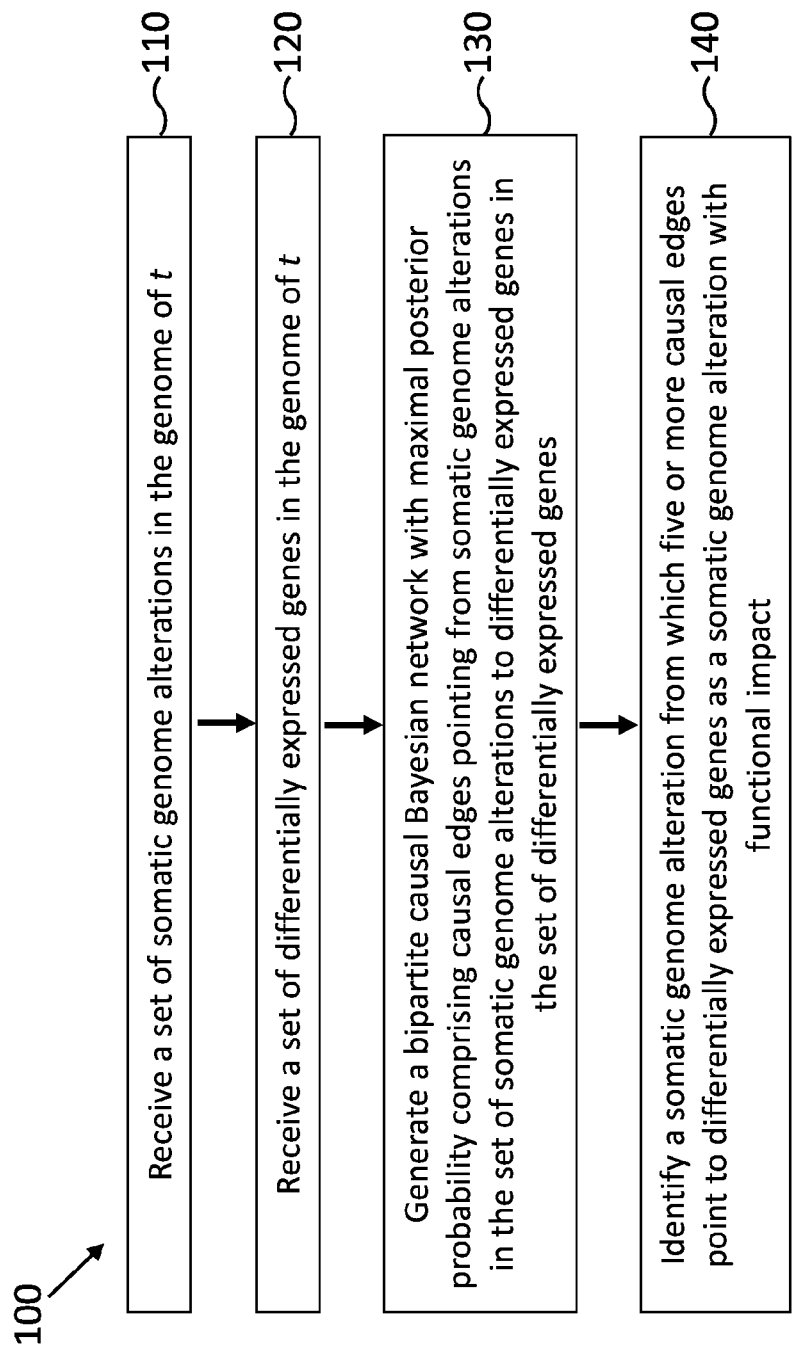
FIG. 11 shows a flow chart illustrating an embodiment of the TDI method for identifying a SGA-FI in the genome of a tumor.

FIG. 11 depicts an exemplary method 100 for identifying a SGA-FI in a tumor, t. The disclosed method infers the functional-impact relationships between SGAs and DEGs for a given tumor using a CBN, in which causal edges are only allowed to point from SGAs to DEGs. Using this method, it is possible for the first time to interrogate a tumor sample and elucidate the SGAs in the tumor genome that cause the phenotype of the tumor, such as malignancy. The tumor genome can be, for example, the genomic sequence determined from a tumor sample from a subject.

As shown in FIG. 11 at process block 110, the method begins by receiving a set of SGAs in the genome of the tumor, t. The set of SGAs includes genes in the genome of the tumor t that contain SMs or that are affected by SCNA within the tumor genome, or both.

At process block 120, the method comprises receiving a set of DEGs in the genome of the tumor, t. The set of set of DEGs includes genes in the genome of tumor t that have increased or decreased expression relative to a control as discussed in more detail below.

The expression level of the genes in the tumor can be determined, for example, by obtaining microarray data showing the levels of RNA in the tumor. In some embodiments, if the expression of the genes follows Gaussian distribution in normal cells, the p values of corresponding genes in the tumor can be calculated to evaluate how significant the gene expression in cells of the tumor is different from that of corresponding non-tumor cells. In some embodiments, a gene is included in the set of DEGs if the p value is equal or smaller than 0.005 to either side of the Gaussian distribution. Additionally, for genes whose expression do not follow Gaussian distribution in normal samples (for example, due to low variance (i.e., <0.1)), the expression fold change can be calculated (for example, the gene expression in the tumor cell over the average gene expression in normal cells). Genes with a 3 fold or greater change in expression in the tumor cell compared to the control can be included in the set of DEGs.

In some embodiments, the method includes obtaining a tumor sample from a subject, identifying DEGs in the genome of the tumor sample (for example, using microarray analysis), and identifying SGAs in the genome of the tumor sample (for example, by sequencing the chromosomal DNA in the tumor sample using whole genome sequencing analysis) to provide the set of SGAs and the set of DEGs.

The tumor sample can be any sample that includes genomic DNA from a tumor cell. Such samples include, but are not limited to, tissue from biopsies (including formalin-fixed paraffin-embedded tissue), autopsies, and pathology specimens; sections of tissues (such as frozen sections or paraffin-embedded sections taken for histological purposes); body fluids, such as blood, or fractions thereof such as plasma or serum, and so forth. In several embodiments, the tumor sample is from an individual suspected of having a cancer.

At process block 130, the method comprises generating a CBN with maximal posterior probability from the sets of SGAs and DEGs. The CBN includes causal edges pointing from SGAs in the set of SGAs to DEGs in the set of DEGs. The result of step 130 is generation of a CBN model M that best explains (that is, has maximal posterior probability) the SGA and DEG data from the tumor t. The CBN model assigns a single SGA in the set of SGAs as the most probable cause for each DEG in the set of DEGs. In model M, a given SGA can have zero, one, or more causal edges emanating from it to the variables in the set of DEGs.

Prior methods for learning Bayesian networks from observations, and computational algorithms to do so, are well understood and have been used successfully in many applications (see, e.g., Glymour C, Cooper G. Computation, Causation, and Discovery. Cambridge, MA: MIT Press; 1999; Friedman, Nir. "Inferring cellular networks using probabilistic graphical models." *Science* 303, no. 5659 (2004): 799-805; and Pe'er, Dana. "Bayesian network analysis of signaling networks: a primer." *Science STKE* 281 (2005): 14). In some embodiments, such prior methods can be modified as described herein to generate the CBN including causal edges pointing from SGAs in the set of SGAs to DEGs in the set of DEGs.

In some embodiments, generating the CBN with maximal posterior probability includes generating a plurality of test CBNs using the sets of SGAs and DEGs from the tumor t. As used herein, a "test CBN" is a CBN that provides a model of the causal relationships between SGAs and DEGs in the current tumor being analyzed. The plurality of test CBNs forms a "search space" from which the CBN with maximal posterior probability is identified. The posterior probability for each test CBN in the plurality is determined, and the test CBN in the plurality with the maximal posterior probability is identified as the CBN with maximal posterior probability.

Determining the posterior probability for the test CBNs in the plurality can be done, for example, by calculating P(D|M)×P(M) for each test CBN, wherein P(D|M) is the marginal likelihood of each test CBN in the plurality (or search space), and P(M) is the prior probability of each test CBN in the plurality (or search space).

In some embodiments, P(M) is proportional to the frequencies at which the SGAs of a test CBN are present in a reference set of tumor genomes, D. The reference set of genomes can be, for example, tumor genomes available from The Cancer Genome Atlas (TCGA). TCGA provides genomic and transcriptomic data from multiple cancer types, providing a systematic characterization of somatic mutations, somatic copy number alterations, oncogenic processes, and for many different types of tumors.

In additional embodiments, P(M) comprises a product of prior probabilities of causal edges of a test CBN. For example, in such embodiments, a prior probability of a causal edge from a somatic alteration of gene $A_h$ to a DEG $E_i$ can be stated as $P(A_h \rightarrow E_i)$ (abbreviated as $\theta_h$) and determined according to:

$$\theta_h = (1 - \theta_0) \frac{\mu_h}{\sum_{h'=1}^{m} \mu_{h'}}$$

wherein $\theta_0$ is a prior probability that the cause of DEG $E_i$ is not a SGA, h' indexes over the number m of genes in tumor t that have SGAs and $\mu_h$ is a Dirichlet parameter set forth as $$\sum_{t' \in U_h} \frac{1}{m_{t'}}$$

wherein $U_h$ denotes tumor genomes in a reference set of tumor genomes, D, that (similar to tumor t) have a somatic alteration in gene $A_h$, and $m_{t'}$ denotes the number of genes with SGAs in the genome of tumor t'. The reference set of tumor genomes, D, is obtained prior to the analysis of the current tumor, and provides a training set of prior tumors. Similarly, $\mu_{h'}$ is a Dirichlet parameter set forth as $$\sum_{t' \in U_{h'}} \frac{1}{m_{t'}}$$

In additional embodiments, known values for the number of unique synonymous mutations in a particular gene in a reference set of tumor genomes D and the number of somatic copy number alterations in the particular gene in subjects without cancer can be applied to account for mutation and copy number alterations that are due to differences in gene lengths and chromosome locations. Thus, in one embodiment, the number of unique synonymous mutations in gene $A_h$ in a reference set of tumor genomes, D, has a known value (a1); the number of somatic copy number alterations in gene $A_h$ in subjects without cancer has a known value (a2); and $\mu_h$ is:

$$\sum_{t' \in U_h} w_{ht'}$$

wherein $U_h$ denotes tumor genomes from a reference set of tumor genomes, D, that have a somatic alteration in gene $A_h$, and $w_{ht'}$ denotes a weight proportional to the probability that the somatic alteration in gene $A_h$ is the SGA with functional impact in the genome of tumor t'. $w_{ht'}$ is calculated as:

$$w_{ht'} = \frac{R_{ht'}}{\sum_{h'=1}^{m} R_{h't'}},$$

wherein $$R_{ht'} = \frac{T_{ht'}^{SM}}{R_h^{SM}} + \frac{T_{ht'}^{SCNA}}{R_h^{SCNA}}.$$

In the above equations, $T_{ht'}^{SM}$ denotes whether gene $A_h$ has a non-synonymous somatic mutation or not in tumor t' (e.g., $T_{ht'}^{SM}$ can be 1 or 0, respectively); $R_h^{SM}$ denotes the number of unique synonymous somatic mutation events in gene $A_h$ in the reference set of tumor genomes, D; $T_{ht'}^{SCNA}$ denotes whether gene $A_h$ has a somatic copy number alteration or not in tumor t' (e.g., $T_{ht'}^{SCNA}$ is 1 or 0, respectively); $R_h^{SCNA}$ denotes the expected number of times gene $A_h$ has a somatic copy number alteration among the tumors in D, and yet is only a passenger alteration (that is, has no functional impact), based on the number of times gene $A_h$ has a somatic copy number alteration in a reference set of genomes from subjects without known cancer (e.g., subjects in the normal human population).

In some embodiments, P (D|M) comprises a product of marginal likelihoods of causal edges of the test CBN for tumor t. Calculating P(D|M) can comprise, for example, calculating a marginal likelihood of each causal edge $A_h \rightarrow E_i$ of the test CBN based on tumor genomes in a reference set of tumor genomes, D, that have the somatic alteration of gene $A_h$ and tumor genomes in D that do not have the somatic alteration of gene $A_h$. The reference set of genomes can be, for example, tumor genomes available from TCGA.

In some embodiments, P (D|M) comprises a product of posterior probabilities of causal edges of the test CBN for tumor t. Calculating P(D|M) can comprise, for example, calculating a posterior probability of each causal edge $A_h \rightarrow E_i$ of the CBN as:

$$\frac{e(h, i)}{\sum_{h'=0}^{m} e(h', i)}$$

wherein:

$$e(h, i) = e(h, i, D_h^1) \cdot e(G(i), i, D_h^0)$$

$$e(h, i, D_h^1) = \theta_h \prod_{j=1}^{q_i} \frac{\Gamma(\alpha_{ij})}{\Gamma(\alpha_{ij} + N_{ij}^1)} \prod_{k=1}^{r_i} \frac{\Gamma(\alpha_{ijk} + N_{ijk}^1)}{\Gamma(\alpha_{ijk})}$$

$$e(G(i), i, D_h^0) = \theta_{G(i)} \prod_{j=1}^{q_i} \frac{\Gamma(\alpha_{ij})}{\Gamma(\alpha_{ij} + N_{ij}^0)} \prod_{k=1}^{r_i} \frac{\Gamma(\alpha_{ijk} + N_{ijk}^0)}{\Gamma(\alpha_{ijk})}$$

In the formulas listed above, $D_h^1$ denotes tumor genomes having the somatic alteration of gene $A_h$ that are present in a reference set of tumor genomes, D; $D_h^0$ denotes tumor genomes that do not have the somatic alteration of gene $A_h$ that are present in D; and G(i) denotes a gene that has a maximal posterior probability for causing $E_i$ in D (or a "global driver"). G(i) can be calculated by finding the gene g that maximizes the following function and assigning G(i) to be g:

$$\theta_g \prod_{j=1}^{q_i} \frac{\Gamma(\alpha_{ij})}{\Gamma(\alpha_{ij} + N_{ij})} \prod_{k=1}^{r_i} \frac{\Gamma(\alpha_{ijk} + N_{ijk})}{\Gamma(\alpha_{ijk})}$$

wherein $N_{ijk}$ is the number of tumor genomes in D, wherein node $E_i$ has value k and its cause $A_g$ has the value denoted by j, and $\theta_g$ denotes the prior probability that $A_g$ is the cause for $E_i$ for the tumor genomes D; j indexes over the states of $A_g$, which is being considered as the cause of $E_i$; $q_i$ is 2; k is an indicator variable which indexes over the states of $E_i$; $r_i$ is 2; $\alpha_{ijk}$ is a parameter in a Dirichlet distribution that is proportional to the prior probability of $P(E_i=k|A_g=j)$; $\Gamma$ is the gamma function; $N_{ij}=\Sigma_k^{r_i} N_{ijk}$; $\alpha_{ij}=\Sigma_k^{r_i} \alpha_{ijk}$; $N_{ijk}^1$ is the number of tumor genomes in $D_h^1$ for which $E_i$ has value k and $A_h$ has the value indexed by j; $N_{ijk}^0$ is the number of tumor genomes in $D_h^0$ for which $E_i$ has value k and $A_{G(i)}$ has the value indexed by j; and wherein $$\theta_g = (1 - \theta_0) \frac{\mu_g}{\sum_{h'=1}^{m} \mu_{h'}}$$

Wherein $\theta_0$ is a prior probability that something other than a SGA is the cause of DEG $E_i$; h' indexes over the number m of genes in tumor t that have SGAs; and $\mu_g$ is a Dirichlet parameter set forth as $$\sum_{t' \in U_g} \frac{1}{m_{t'}}$$

wherein $U_g$ denotes a reference set of tumor genomes that have a somatic alteration in gene $A_g$; and $m_{t'}$ denotes the number of genes with somatic alterations in the genome of tumor t'.

In additional embodiments, known values for the number of unique synonymous mutations in a particular gene in a reference set of tumor genomes D and the number of somatic copy number alterations in the particular gene in subjects without cancer can be applied to account for mutation and copy number alterations that are due to differences in gene lengths and chromosome locations. Thus, in one embodiment, the number of unique synonymous mutations in gene $A_g$ in a reference set of tumor genomes, D, has a known value (a1); the number of somatic copy number alterations in gene $A_g$ in subjects without cancer has a known value (a2); and $\mu_g$ is:

$$\mu_g = \sum_{t' \in U_g} w_{gt'}$$

$w_{gt'}$ is calculated as:

$$w_{gt'} = \frac{R_{gt'}}{\sum_{g'=1}^{m} R_{g't'}},$$

wherein $$R_{gt'} = \frac{T_{gt'}^{SM}}{R_g^{SM}} + \frac{T_{gt'}^{SCNA}}{R_g^{SCNA}}.$$

wherein $U_g$ denotes tumor genomes from a reference set of tumor genomes, D, that have a somatic alteration in gene $A_g$; $m_{t'}$ denotes the number of genes with somatic alterations in the genome of tumor t', and $w_{gt'}$ denotes a weight proportional to the probability that the somatic alterations in gene $A_g$ is the SGA with functional impact in the genome of tumor t'. $w_{gt'}$ is calculated as:

$$w_{gt'} = \frac{R_{gt'}}{\sum_{g'=1}^{m} R_{g't'}},$$

wherein $$R_{gt'} = \frac{T_{gt'}^{SM}}{R_g^{SM}} + \frac{T_{gt'}^{SCNA}}{R_g^{SCNA}}.$$

In the above equations, $T_{gt'}^{SM}$ denotes whether gene $A_g$ has a non-synonymous somatic mutation or not in tumor t' (e.g., $T_{gt'}^{SM}$ is 1 or 0, respectively); $R_g^{SM}$ denotes the number of unique synonymous mutations in gene $A_g$ in the reference set of tumor genomes, D; $T_{gt'}^{SCNA}$ denotes whether gene $A_g$ has a somatic copy number alteration or not in tumor t' (e.g., $T_{gt'}^{SCNA}$ is 1 or 0, respectively); $R_g^{SCNA}$ denotes the expected number of times $A_g$ has a somatic copy number alteration among the tumors in D, and yet is only a passenger alteration (that is, has no functional impact), based on the number of times gene $A_h$ has a somatic copy number alteration in a reference set of genomes from subjects without known cancer (e.g., subjects in the normal human population).

Causal edges from different SGAs have different distributions of posterior probabilities. To standardize how to interpret the significance of an edge probability $P_e$, a random dataset was created by permuting DEG data in reference genomes across tumors such that the statistical relationships between SGAs and DEGs were random in this dataset. The TDI method was applied to this dataset to calculate posterior probability of edges using the permuted data, and the values were treated as samples from a distribution of random posterior probabilities of edges point from a given SGA to DEGs. Given a posterior probability for a causal edge from real data ($P_e$), the probability that an edge from an SGA can be assigned with a given $P_e$ or higher in data from permutation experiments (i.e., the p value to the edge with a given $P_e$) is determined based on the random samples. As shown at process block 140 in FIG. 11, an SGA of the CBN with maximal posterior probability is identified as a SGA-FI in the tumor if five or more causal edges point from the SGA to DEGs in the CBN. In several embodiments, the SGA is identified as an SGA-FI if it has 5 or more causal edges to DEGs that are each assigned a p-value<0.001. In several embodiments, the identified SGA-FI is a driver SGA. As discussed in the examples and shown in FIG. 9, the overall false discovery rate of the joint causal relationships between an SGA to 5 or more target DEGs is less than or equal to $10^{-15}$, effectively controlling the false discovery when identifying SGA-FIs in a tumor.

Once the SGA-FIs impact are identified, the information can be used in downstream applications, for example, to select a treatment for tumor t in a subject, or to provide a diagnosis or prognosis concerning the subject with tumor t. Providing a diagnosis or prognosis concerning the subject with tumor t can include, for example, predicting the outcome (for example, likelihood of aggressive disease, recurrence, metastasis, or chance of survival) and sensitivity to molecularly targeted therapy of the subject.

Computer Implementation

The analytic methods described herein can be implemented by use of computer systems. For example, any of the steps described above for identifying a SGA-FI may be performed by means of software components loaded into a computer or other information appliance or digital device. When so enabled, the computer, appliance or device may then perform all or some of the above-described steps to assist the analysis of values associated with the For example, any of the steps described above for identifying a SGA-FI may be performed by means of software components loaded into a computer or other information appliance or digital device. The above features embodied in one or more computer programs may be performed by one or more computers running such programs.

Aspects of the disclosed methods for identifying a SGA-FI can be implemented using computer-based calculations and tools. For example, a CBN model can be generated by a computer based on underlying sets of SGAs and DEGs from a tumor. The tools are advantageously provided in the form of computer programs that are executable by a general purpose computer system (for example, as described in the following section) of conventional design.

Computer code for implementing aspects of the present invention may be written in a variety of languages, including PERL, C, C++, Java, JavaScript, VBScript, AWK, or any other scripting or programming language that can be executed on the host computer or that can be compiled to execute on the host computer. Code may also be written or distributed in low level languages such as assembler languages or machine languages. The host computer system advantageously provides an interface via which the user controls operation of the tools.

Any of the methods described herein can be implemented by computer-executable instructions in (e.g., encoded on)

one or more computer-readable media (e.g., computer-readable storage media or other tangible media). Such instructions can cause a computer to perform the method. Any of the methods described herein can be implemented by computer-executable instructions stored in one or more computer-readable storage devices (e.g., memory, magnetic storage, optical storage, or the like). Such instructions can cause a computer to perform the method.

Example Computing System

Figure 12:
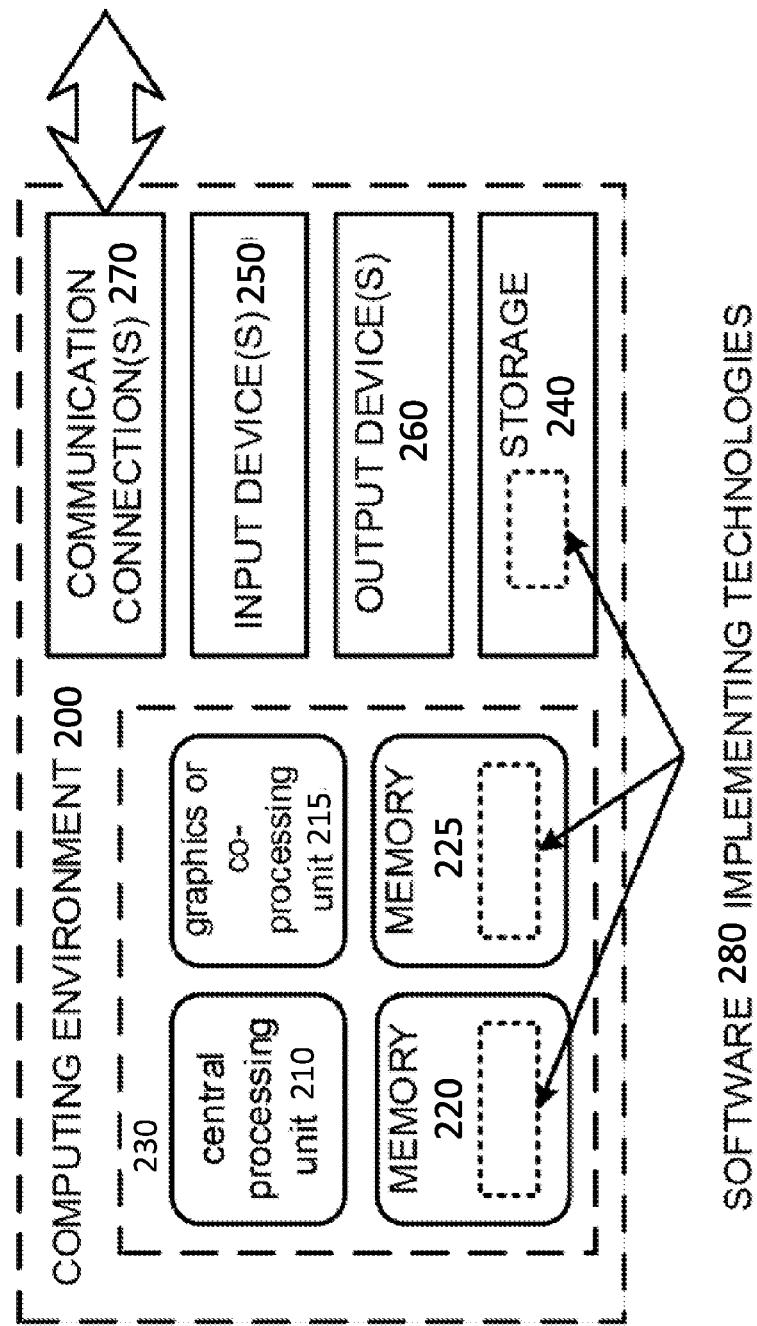
FIG. 12 shows a diagram of an example computing system in which described embodiments can be implemented.

FIG. 12 illustrates a generalized example of a suitable computing system 200 in which several of the described innovations may be implemented. The computing system 200 is not intended to suggest any limitation as to scope of use or functionality, as the innovations may be implemented in diverse computing systems, including special-purpose computing systems. In practice, a computing system can comprise multiple networked instances of the illustrated computing system.

With reference to FIG. 12, the computing system 200 includes one or more processing units 210, 215 and memory 220, 225. In FIG. 12, this basic configuration 230 is included within a dashed line. The processing units 210, 215 execute computer-executable instructions. A processing unit can be a central processing unit (CPU), processor in an application-specific integrated circuit (ASIC), or any other type of processor. In a multi-processing system, multiple processing units execute computer-executable instructions to increase processing power. For example, FIG. 12 shows a central processing unit 210 as well as a graphics processing unit or co-processing unit 215. The tangible memory 220, 225 may be volatile memory (e.g., registers, cache, RAM), non-volatile memory (e.g., ROM, EEPROM, flash memory, etc.), or some combination of the two, accessible by the processing unit(s). The memory 220, 225 stores software 280 implementing one or more innovations described herein, in the form of computer-executable instructions suitable for execution by the processing unit(s).

A computing system may have additional features. For example, the computing system 200 includes storage 240, one or more input devices 250, one or more output devices 260, and one or more communication connections 270. An interconnection mechanism (not shown) such as a bus, controller, or network interconnects the components of the computing system 200. Typically, operating system software (not shown) provides an operating environment for other software executing in the computing system 200, and coordinates activities of the components of the computing system 200.

The tangible storage 240 may be removable or non-removable, and includes magnetic disks, magnetic tapes or cassettes, CD-ROMs, DVDs, or any other medium which can be used to store information in a non-transitory way and which can be accessed within the computing system 200. The storage 240 stores instructions for the software 280 implementing one or more innovations described herein.

The input device(s) 250 may be a touch input device such as a keyboard, mouse, pen, or trackball, a voice input device, a scanning device, or another device that provides input to the computing system 200. For video encoding, the input device(s) 250 may be a camera, video card, TV tuner card, or similar device that accepts video input in analog or digital form, or a CD-ROM or CD-RW that reads video samples into the computing system 200. The output device(s) 260 may be a display, printer, speaker, CD-writer, or another device that provides output from the computing system 200.

The communication connection(s) 270 enable communication over a communication medium to another computing entity. The communication medium conveys information such as computer-executable instructions, audio or video input or output, or other data in a modulated data signal. A modulated data signal is a signal that has one or more of its characteristics set or changed in such a manner as to encode information in the signal. By way of example, and not limitation, communication media can use an electrical, optical, RF, or other carrier.

The innovations can be described in the general context of computer-executable instructions, such as those included in program modules, being executed in a computing system on a target real or virtual processor. Generally, program modules include routines, programs, libraries, objects, classes, components, data structures, etc. that perform particular tasks or implement particular abstract data types. The functionality of the program modules may be combined or split between program modules as desired in various embodiments. Computer-executable instructions for program modules may be executed within a local or distributed computing system.

For the sake of presentation, the detailed description uses terms like "determine" and "use" to describe computer operations in a computing system. These terms are high-level abstractions for operations performed by a computer, and should not be confused with acts performed by a human being. The actual computer operations corresponding to these terms vary depending on implementation.

Computer-Readable Media

Any of the methods described herein can be implemented by computer-executable instructions in (e.g., stored on, encoded on, or the like) one or more computer-readable media (e.g., computer-readable storage media or other tangible media) or one or more computer-readable storage devices (e.g., memory, magnetic storage, optical storage, or the like). Such instructions can cause a computing device to perform the method. The technologies described herein can be implemented in a variety of programming languages.

Any of the computer-readable media herein can be non-transitory (e.g., volatile memory such as DRAM or SRAM, nonvolatile memory such as magnetic storage, optical storage, or the like) and/or tangible. Any of the storing actions described herein can be implemented by storing in one or more computer-readable media (e.g., computer-readable storage media or other tangible media). Any of the things (e.g., data created and used during implementation) described as stored can be stored in one or more computer-readable media (e.g., computer-readable storage media or other tangible media). Computer-readable media can be limited to implementations not consisting of a signal.

EXAMPLES

The following examples are provided to illustrate particular features of certain embodiments, but the scope of the claims should not be limited to those features exemplified.

Example 1

Identifying Cancer Drivers by Inferring Tumor-Specific Causal Relationships Between Somatic Genome Alterations and Molecular Phenotypes This example illustrates a method of delineating the causal relationships between SGAs and observed molecular phenotypes as a means to reveal SGAs that likely contribute to the development of a tumor. For example, a tumor t hosts a set of SGAs, denoted as SGA_SET$_t$, and a set of DEGs, designated as DEG_SET$_t$. The TDI method represents the causal relationships between SGAs and DEGs as a CBN (see FIG. 1) and searches for the model with the maximal posterior probability P(M|D) that best explains the data (SGAs and DEGs) of tumor t.

The TDI method combines the strengths of both frequency- and functional-impact oriented approaches for identifying driver SGAs. The TDI method uses the frequency with which a gene g is perturbed by SGA events in a reference set of tumor genomes, D, to estimate the prior probability P(g) that g is a cancer driver in any given tumor. To further incorporate information from a function-impact perspective, TDI employs the likelihood function P(data|g), which represents the probability of the molecular phenotype data that is observed (e.g., DEGs) given that g is assumed to be a driver. From such priors and likelihoods, TDI derives the posterior probabilities of drivers for a given tumor. By inferring causal relationships between SGA events and molecular phenotypes, TDI can identify cancer drivers and provide insight into the disease mechanism of individual tumors.

Results

The TDI method was used to analyze data from 4,468 tumors across 16 cancer types in TCGA to derive 4,468 tumor-specific models. An SGA was designated as an SGA with functional impact (SGA-FI) in a specific tumor if it is predicted by TDI to causally regulate 5 or more DEGs in the tumor with an expected false discovery rate $\leq 10^{-15}$. Since it is statistically difficult to evaluate whether the driver identified within an individual tumor is valid, the results from multiple tumors were pooled to evaluate whether the causal relationship between a pair of SGA and DEG are conserved across tumors and further performed biological experiments to validate predictions by TDI.

The Landscape of Candidate Cancer Drivers Identified Using the TDI Method.

Figure 2B:
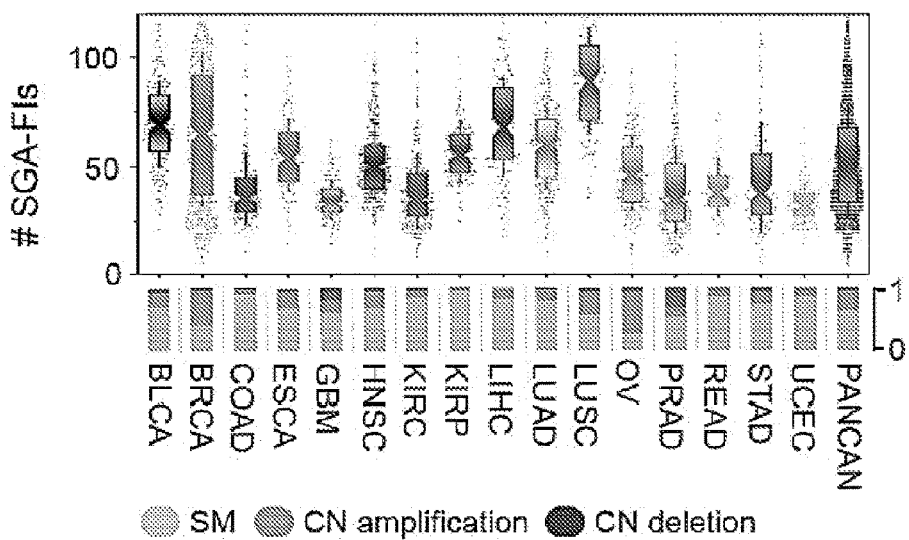
Figure 2C:
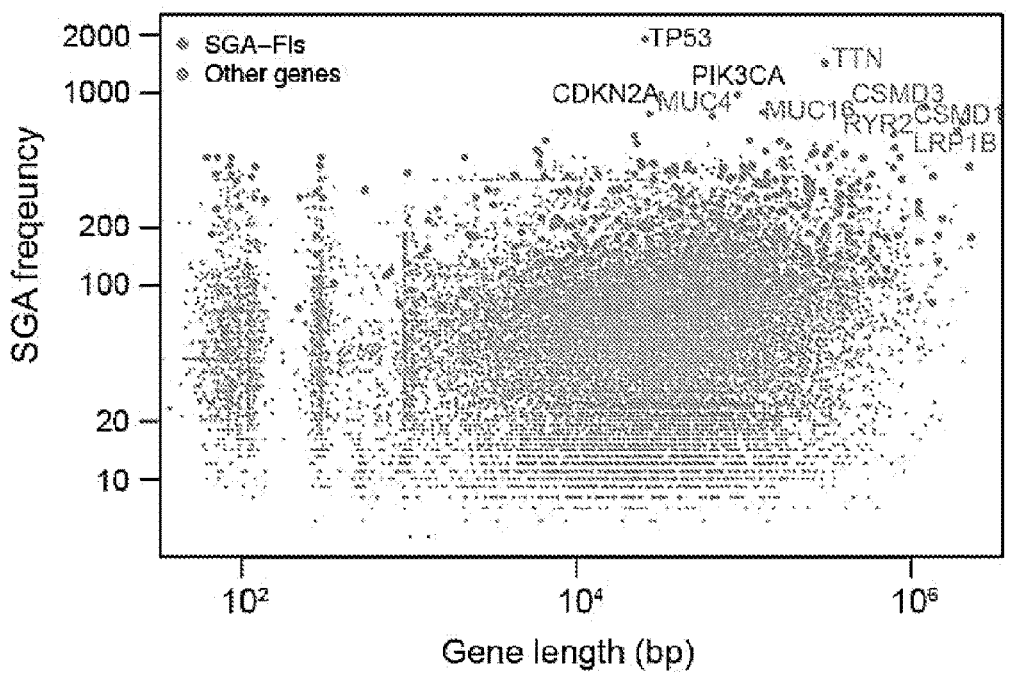

First the landscape of SGA-FIs was investigated. SGAs were organized according to the genes perturbed by them and represented each SGA by the corresponding gene names. The distribution of the number of SGAs and SGA-FIs per tumor was compared across cancer types (FIGS. 2A-2B). The average number of SGAs per tumor across cancer types was approximately 500, whereas the average number of SGA-FIs identified by TDI was approximately 50 per tumor. TDI identified 490 SGAs that had a significant functional impact in more than 1% of the tumors; these SGAs include the majority (86.1%) of the known drivers published by the TCGA network (see Kandoth et al, Nature, 502, 333-339, 2013; and Lawrence et al, Nature, 505, 495-501, 2014) as well as novel candidate drivers. SGA-FIs identified by TDI include protein encoding genes as well as microRNAs and intergenic non-protein-coding RNAs (e.g., MIR548K, MIR1207, and PVT1). Being a functional impact-oriented model, TDI can identify SGA-FIs independent of their alteration frequency or gene length (FIG. 2C). In addition, many SGAs with similar alteration frequency or gene length as those designated as SGA-FIs by TDI are not called as SGA-FIs by TDI, further demonstrating that TDI predictions are not simply a function of alteration frequency or gene length.

Figure 2D:
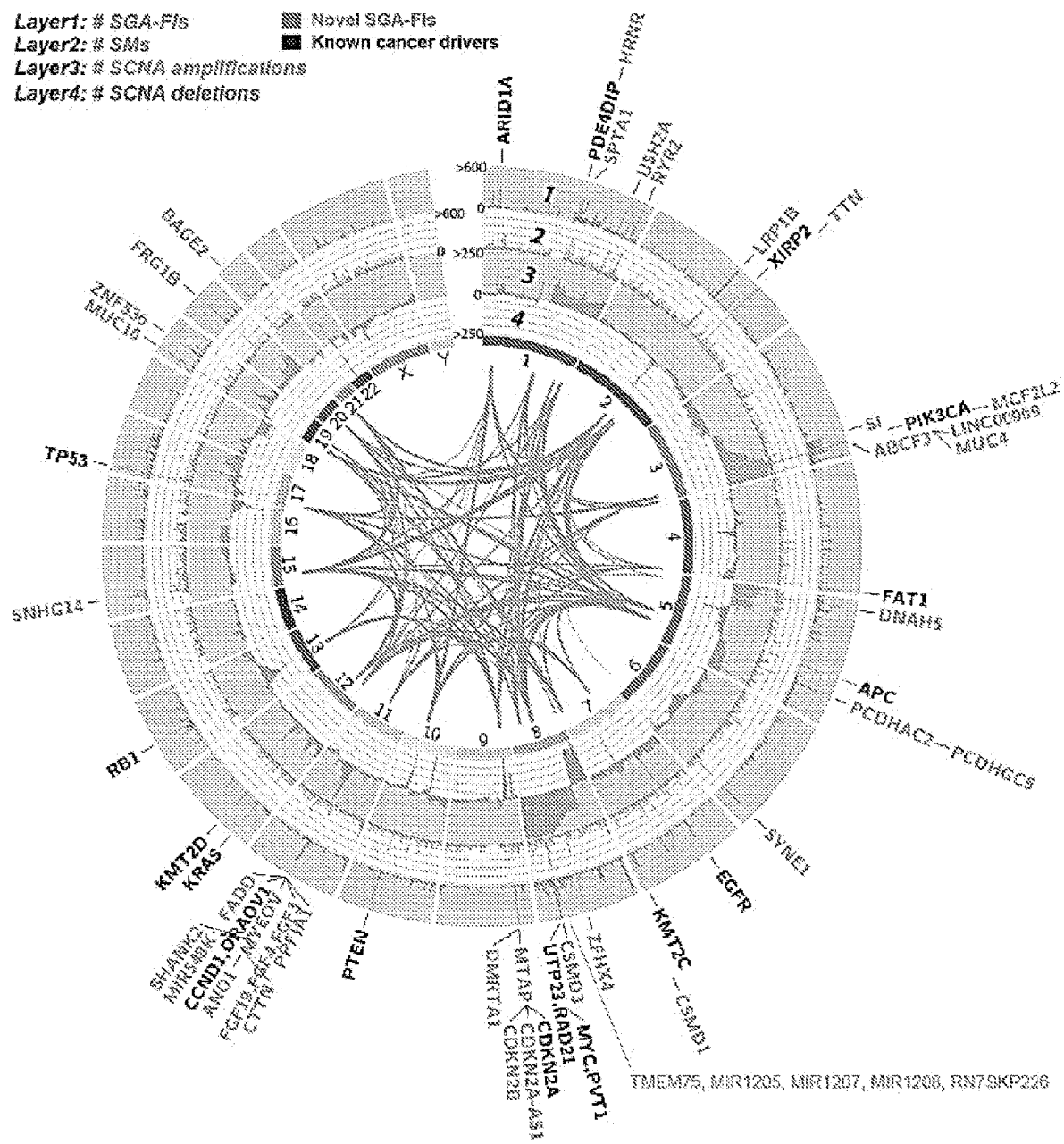
Figure 2E:
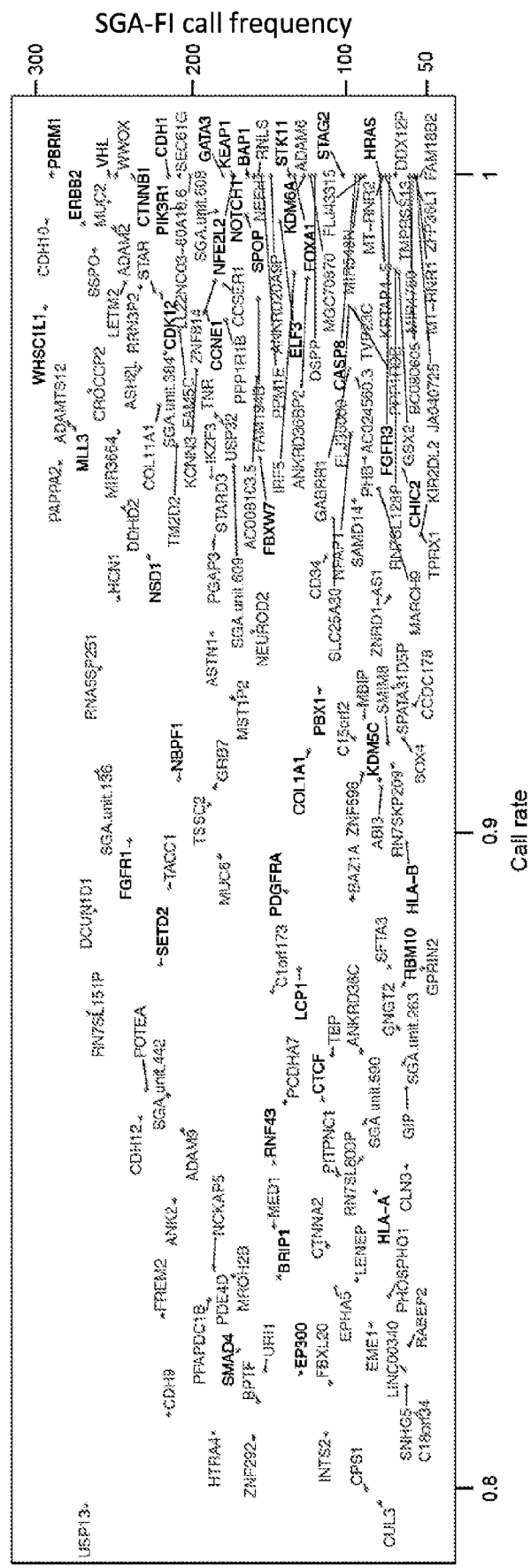

The landscape of common SGAs and SGA-FIs is illustrated (FIG. 2D) using a Circos plot (circos.ca) that includes 62 SGA-FIs that occurred in more than 300 tumors (>6% of the tumors) and that also have a call rate (the fraction of the SGA instances affecting a gene being called an SGA-FI) greater than or equal to 0.8. TDI also designated many low-frequency SGAs (less than 300 tumors or less than 7%) as SGA-FIs with high call rates ($\geq 0.8$) (FIG. 2E). TDI designated as SGA-FIs both well-known drivers (e.g., TP53, PIK3CA, PTEN, KRAS, and CDKN2A) and more controversial (e.g., TNN, CSMD3, MUC16, LRP1B, and ZFHX4) drivers.

Causal Relationships Inferred by TDI are Statistically Robust.

Whether the causal relationships between SGAs and DEGs inferred by TDI as SGA-FIs are statistically robust was evaluated. A series of random datasets using the TCGA data were generated, in which the DEG status of each gene expression variable was permuted across tumors, while the SGA status in each tumor remained as reported by TCGA. As such, the statistical relationships between SGAs and DEGs would be expected to be random. TDI was applied to these random datasets to calculate the posterior probabilities for the candidate causal edges in these permuted tumor data, and compared the distributions of the posterior probabilities assigned by TDI to all candidate edges in the real and the random data.

TDI was able to differentiate statistical relationships between SGAs and DEGs from random ones (FIG. 3A) in that it generally assigned much higher posterior probabilities to candidate edges obtained from real data than those obtained from random data. A large number of edges from well-known transcriptomic regulators (e.g., PIK3CA3) were assigned high posterior probabilities. Interestingly, the results also show more causal edges to DEGs from TTN, CSMD3, MUC16, RYR2, LRP1B, and ZFHX4, with higher posterior probabilities than would be expected by random chance, indicating that perturbing any of these genes has transcriptomic impact (FIG. 3A). Overall, the results from these randomization experiments indicate that the causal relationships inferred by TDI are statistically sound.

An SCNA event (amplification or deletion of a chromosome fragment) in a tumor often encloses a large number of genes, making it a challenge to detect the distinct signals perturbed by individual genes within a SCNA fragment. TDI addresses this problem by integrating both SM and SCNA data, which can create a "linkage disequilibrium" among genes within a SCNA fragment (FIG. 3B). For example, the chromosome cytoband 3q26 enclosing PIK3CA is commonly amplified, and it would be difficult to distinguish the signal of amplification of PIK3CA from those of the other genes within this fragment based on SCNA data alone. However, when combined with SM data, PIK3CA clearly has a higher combined alteration rate than its neighbor genes, making it uncorrelated (as illustrated by darker blue) with its neighbor genes (FIG. 3B). During the process of calculating whether PIK3CA amplification is causally responsible for a DEG observed in a specific tumor, TDI uses the statistics collected from all tumors with PIK3CA alterations (combining SM and SCNA) to calculate the likelihood that such a causal relationship is preserved in the tumor, enabling it to differentiate the signals perturbed by PIK3CA from those of the other genes in the same SCNA fragment. It can be noted that alteration of CSMD3 and ZFHX4 exhibit similar patterns, enabling TDI to detect their distinct signals (FIG. 3B).

Causal Relationships Inferred by TDI are Biologically Sensible.

Figure 4A:
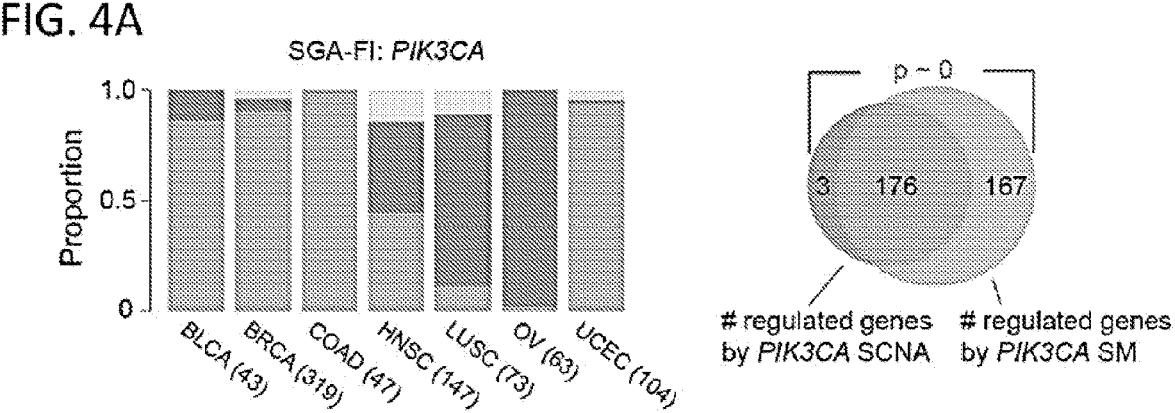
FIGS. 4A-4C illustrate that an SM and a SCNA perturbing a gene exert a common functional impact. The SGA patterns for 3 genes, PIK3CA, CSMD3, and ZFHX4, across different cancer types are shown on the left side. Venn diagrams illustrating the relationships of DEGs caused by SCNA (dark grey) and SM (light grey) are shown on the right side. The p-values were calculated using the Fisher's exact test.

A driver gene can be perturbed due to different SGA events (e.g., SMs, SCNAs, or both) and cancer types vary in the number of each type of alteration exhibited. For example, in the dataset used here (FIG. 4), PIK3CA is commonly altered by SMs in breast cancer, whereas it is mainly altered by SCNAs in ovarian cancer and is almost equally altered by SMs and SCNAs in head and neck squamous carcinoma. As a well-known cancer driver in many cancer types, PIK3CA amplification and mutations should share a common functional impact.

Figure 4B:
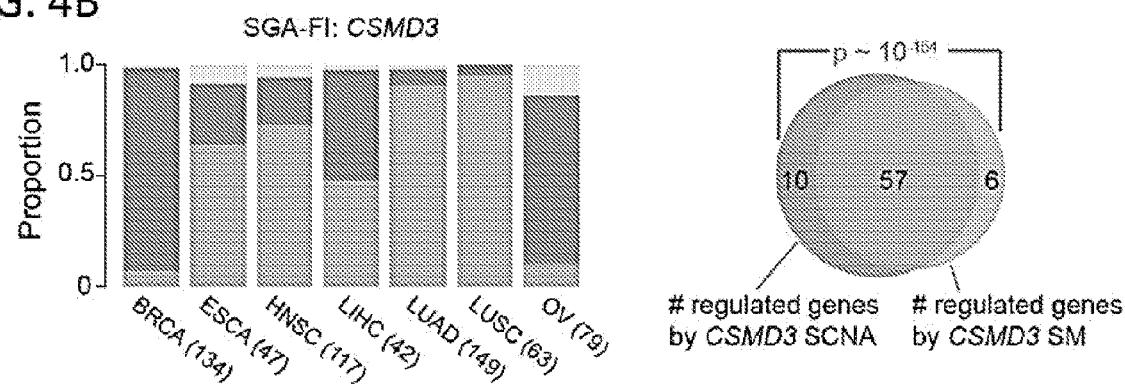
Figure 4C:
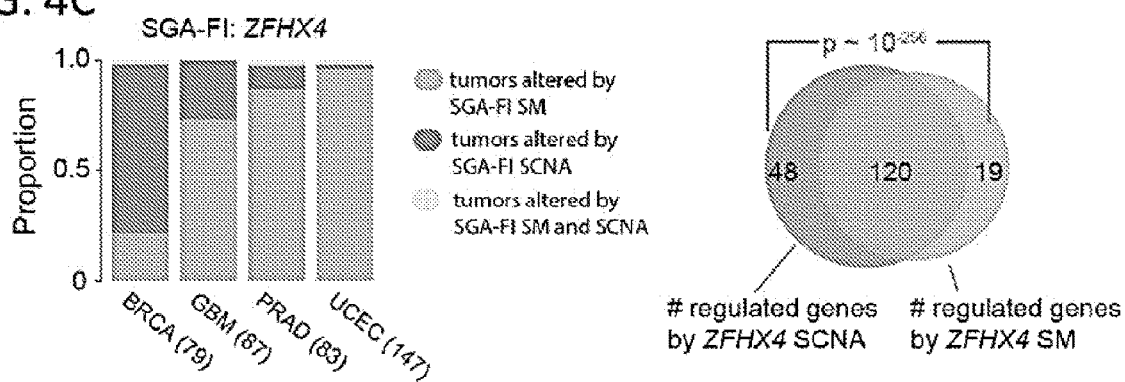

The target DEGs regulated by each SGA event in PIK3CA (SM or SCNA) were identified in individual tumors, and the lists of DEGs that were predicted to be caused by SMs and SCNAs significantly overlap ($p<10^{-100}$, Fisher's exact test). Thus, TDI correctly detected the shared functional impact of PIK3CA when perturbed by different types of SGAs in different cancer types. Similar results were obtained for 157 SGA-FIs that were commonly perturbed by both SMs and SCNAs (with each type accounting for >30% of instances for each SGA-FI), including CSMD3 and ZFHX4 (FIGS. 4B and 4C).

Additionally, whether the TDI-inferred causal relationships between SGAs and DEGs agree with existing knowledge was evaluated. For example, because RB1 protein regulates the transcription factor E2F1, E2F1-regulated genes should be enriched among the RB1-targeted DEGs predicted by TDI. The PASTAA program (trap.mol-gen.mpg.de/PASTAA.htm) was used to search for motif binding sites in the promoters of the 164 DEGs that TDI predicted to be regulated by RB1 and found E2F1 binding sites in the promoters of 116 of these ($p<10^{-100}$).

In addition, an SGA was represented as a vector reflecting the profile of its target DEGs (a vector spanning the DEG space), in which an element reflect the number of tumors in which the SGA is predicted by TDI to regulate a DEG, and the pair-wise similarity (closeness in DEG space) of SGAs was evaluated. The KEAP1-NFE2F2 pair were among the closest SGAs with DEGs that significantly overlapped ($p<10^{-52}$), agreeing with the knowledge that KEAP1 regulates the function of NFE2F2. These results indicate that the functional impacts inferred by TDI are biologically sensible.

TDI Analyses Reveal Functional Connections Among SGA-FIs

Identification of DEGs that are functionally impacted by SGAs can suggest whether different SGAs perturb a common signal. All pair-wise intersections between target DEG sets of SGA-FIs were evaluated to identify SGA pairs sharing significantly overlapping target DEGs ($p<10^{-3}$, Fisher's exact test). SGA-FIs that perturb common signals in a network were then organized, in which an edge connecting a pair of SGA-FI nodes indicates that their target DEG sets significantly overlap.

Within the results, SGA-FIs were identified that belong to two well-known cancer pathways, the p53 pathway and the Notch1 pathway from the Kyoto Encyclopedia of Genes and Genomes (KEGG), and these were connected in networks based on their shared target DEGs (FIG. 5A). Indeed, the members of these two pathways are densely connected and share common functional impacts. Through the created network graph, novel candidate drivers were found that are highly connected to the well-known members of these pathways, which provides the means to evaluate the potential oncogenic properties of candidate SGA-FIs.

Figure 8:
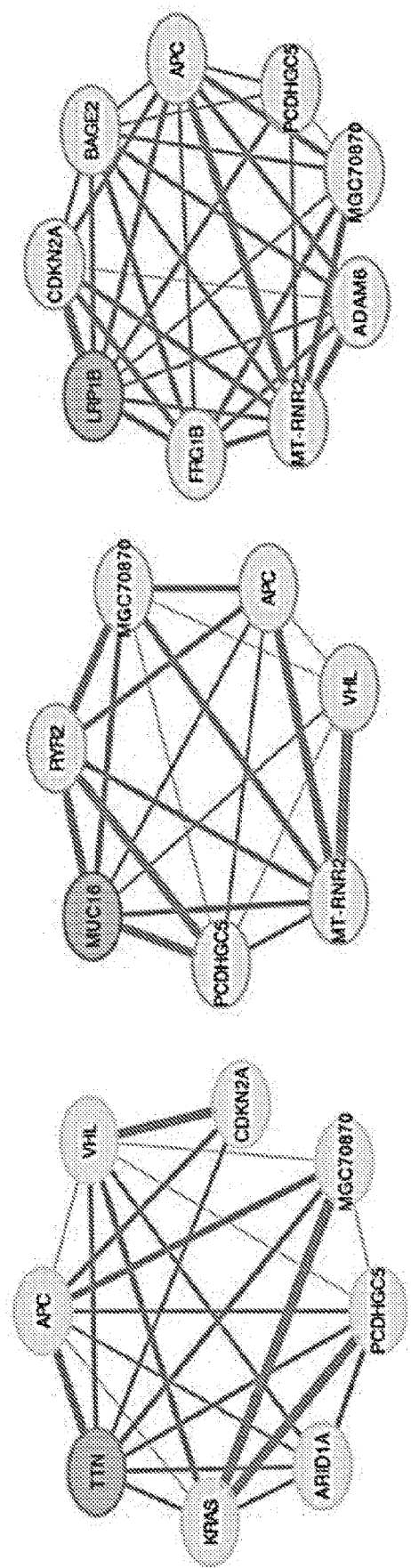
FIG. 8 shows that networks of SGA-FIs share significantly overlapping DEGs. Top SGA-FIs that share the most significant overlapping target DEGs with 3 SGA-FIs (TTN, MUC16, and LRP1B). An edge between a pair of SGA-FIs indicates that they share significantly overlapping target DEG sets (hypergeometric test $p \leq 10^{-6}$), and the thickness of the line is proportional to the negative log of the hypergeometric p-values of overlapping target DEG sets.

The top five (ranked according to p-value significance) SGA-FIs were identified that share significant overlapping target DEGs with an SGA-FI and connected them as a network. For example, the top five SGAs that share DEGs with PIK3CA include PTEN, TP53, and GATA3, which are known cancer drivers, and their connections agree with existing knowledge. The top five SGA-FIs connected with CSMD3 and ZFHX4 (FIG. 5B) also form densely connected networks that include well-known cancer drivers, such as TP53, KRAS, and APC, suggesting that alteration of CSMD3 and ZFHX4 perturb some of the same signaling pathways. We found similar results for other common SGA-FIs, including TTN, MUC16, and LRP1B (FIG. 8).

Cellular Experiments Provide Support for ZFHX4 and CSMD3 as Cancer Drivers

Figure 6C:
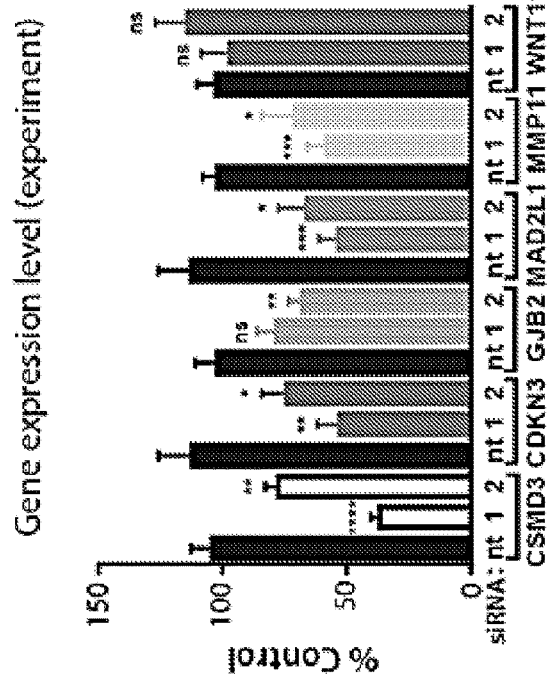
FIGS. 6A-6I illustrate the cell biology evaluation of oncogenic properties of CSMD3 and ZHFX4. 6A & 6B. Expression status of CSMD3 and ZHFX4 target genes in tumors with or without alteration in the respective genes. 6C & 6D. The impact of knocking down CSMD3 and ZHFX4 on the expression of their target genes. For each cell line, we applied a tailored pair of siRNAs (indicated as 1 and 2); (ns: not significant; * $p<0.05$;  $p<0.01$; and * $p<0.001$, **** $p<0.0001$). 6E-6H. The impact of knocking down CSMD3 and ZFHX4 on cell proliferation (6E & 6F) and cell migration (6G & 6H). 6I. Impact of ZFHX4 knockdown on apoptosis in the PC3 cell line as measured by flow cytometry using Annexin V staining (to access apoptotic cells) and propidium iodide (PI) staining (to assess cellular viability) staining, where the pseudo-color of a point indicates the proportion of cells with corresponding values of two markers, and the range of color from blue to red indicate increasing proportion.
Figure 6D:
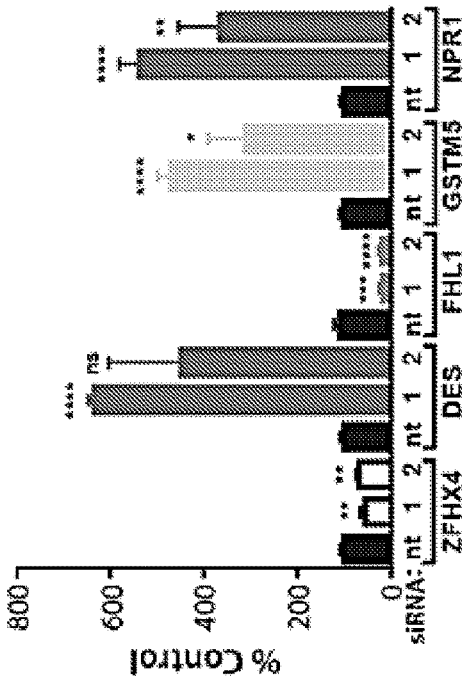
Figure 6A:
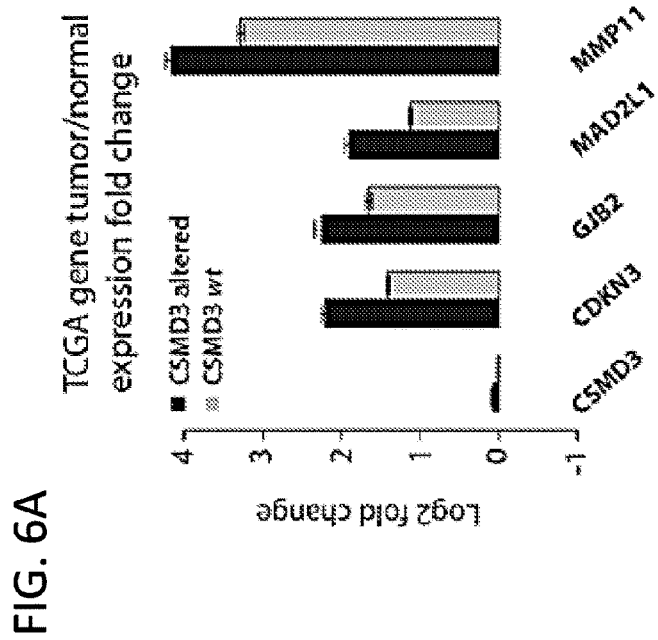
Figure 6B:
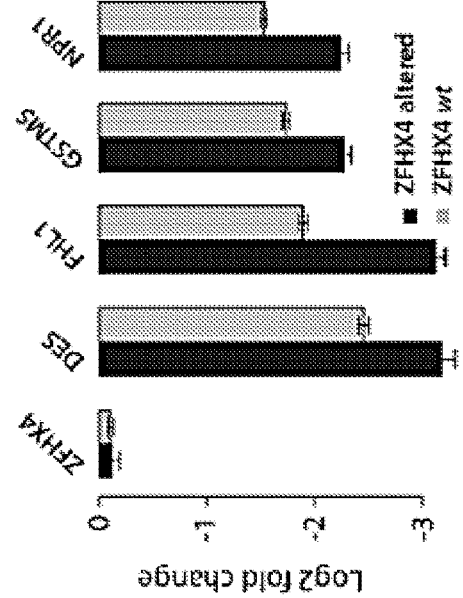
Figure 6E:
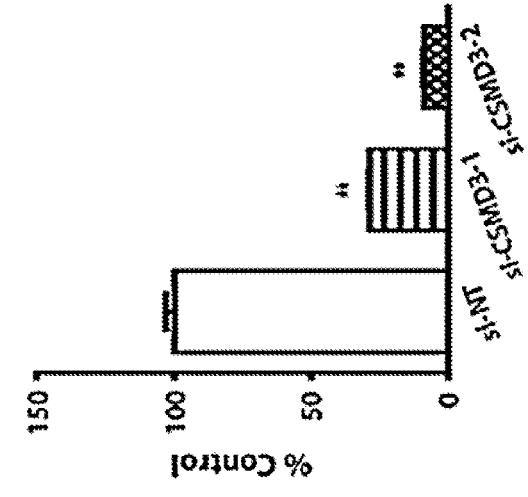
Figure 6G:
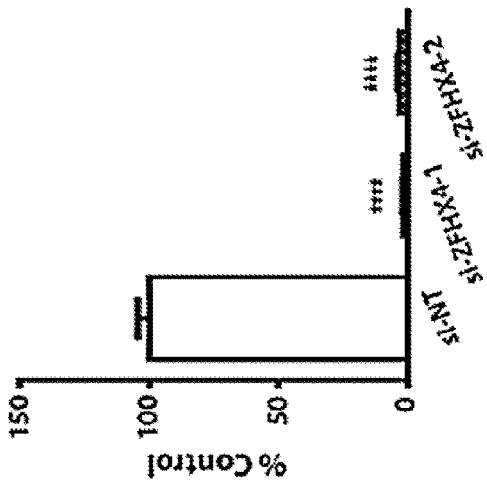
Figure 6F:
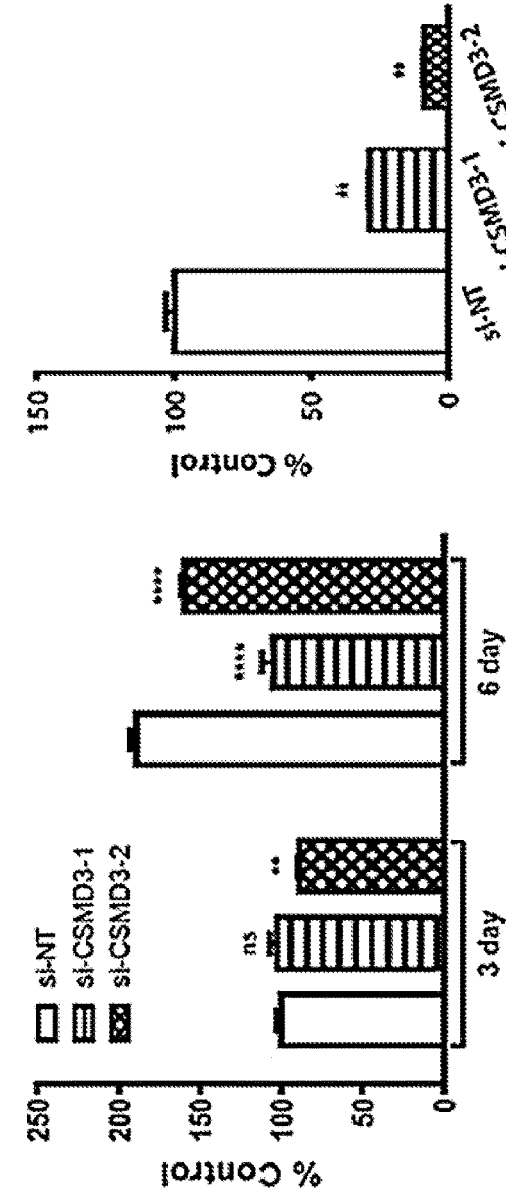
Figure 6H:
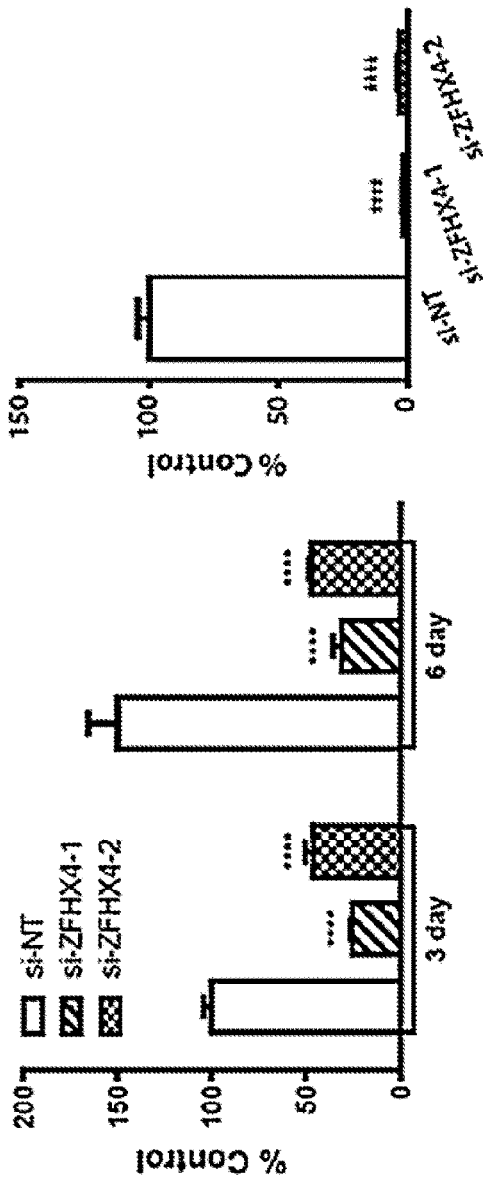

The results of TDI analyses indicate that commonly observed SGAs, including TTN, CSMD3, MUC16, and ZFHX4, have a functional impact on many DEGs in tumor, even though they are not commonly considered to be cancer drivers. The predicted causal relationships between CSMD3 and ZFHX4 and target DEGs were evaluated experimentally by testing their impact on cellular behavior in cancer cell lines. Both CSMD3 and ZFHX4 are very long genes, and they are often perturbed by both SMs and SCNAs, but these SGAs are commonly deemed as passenger events. Whether manipulating these genes in cell lines causally affects their target DEGs, as predicted by TDI, was also examined The top five DEGs most frequently designated as the targets of CSMD3 (CDKN3, GJB2, MADL2, MMP11, WNT11) and of ZFHX4 (DES, NPR1, CDCA3, GSTM5, FHL1) were selected. Four of the five DEGs of CSMD3 are overexpressed in tumors (FIG. 6A) relative to normal tissue of the same type, suggesting their overexpression was positively selected. The five selected DEGs that are targeted by ZFHX4 were suppressed in tumors compared with normal tissue (FIG. 6B). A gastric cancer cell line (HGC27) was identified with CSMD3 amplification and a prostate cancer cell line (PC3) with ZFHX4 amplification. We performed RNAi-mediated gene silencing experiments using multiple siRNAs targeting different regions of CSMD3 and ZFHX4 transcripts. Knocking down CSMD3 resulted in significant repression of four overexpressed target DEGs, with WNT11 being non-significant (FIG. 6C). Knocking down ZFHX4 resulted in significant induction of three target DEGs (DES, GSTM5, and NPR1) (FIG. 6D); CDCA3 was not expressed in the PC3 cell line, and FHL1 was further repressed. While preliminary, these results support that the SGA-FIs inferred by TDI have a biological influence on their associated DEGs.

Figure 6I:
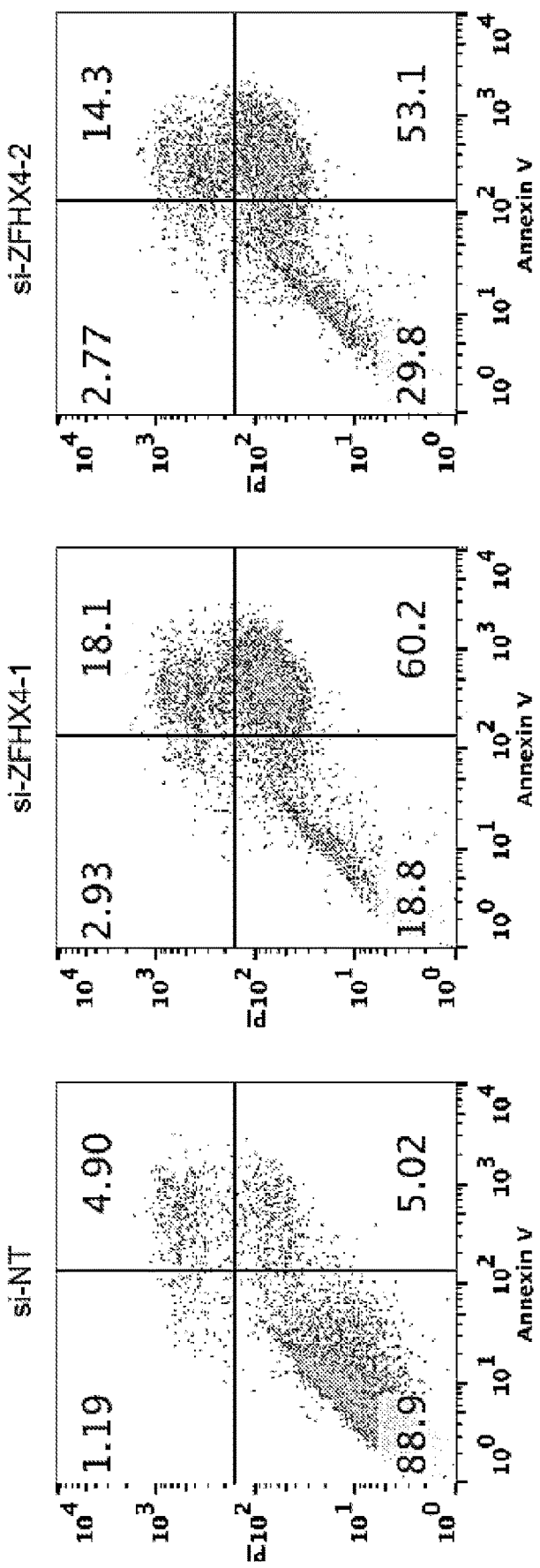
Figure 7A:
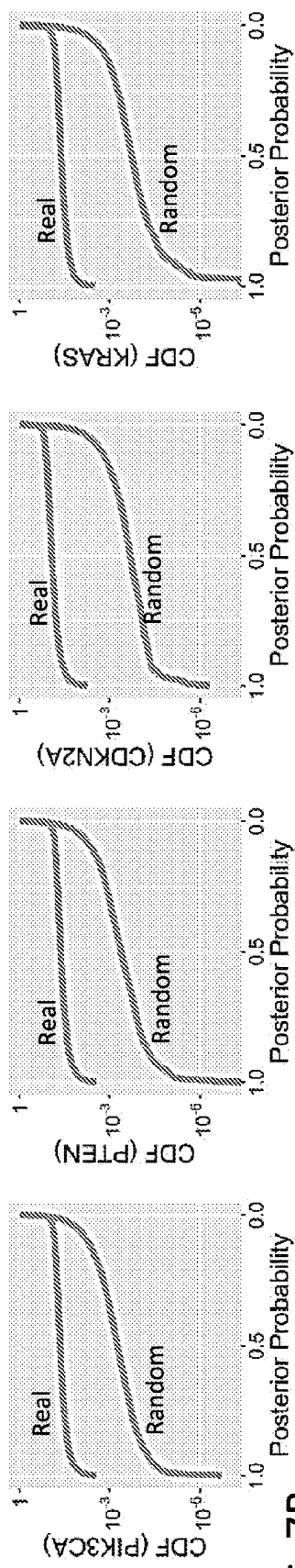
FIGS. 7A and 7B illustrate a comparison of causal analysis results from real data and random data. 7A. Comparison of cumulative distributions of the posterior probabilities of the candidate causal edges point from 4 well-known cancer drivers to DEGs. 7B. Comparison of cumulative distributions of the posterior probabilities of the candidate causal edges point from 4 novel candidate drivers to DEGs.
Figure 7B:
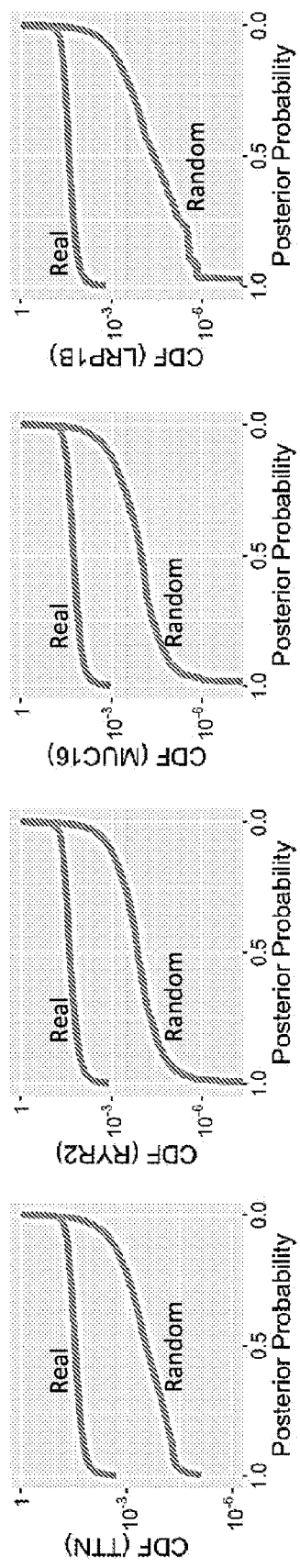

We also examined whether alteration of CSMD3 and ZFHX4 expression affected oncogenic phenotype. The experimental results indicate that knocking down CSMD3 and ZFHX4 in the respective cell lines significantly attenuated cell proliferation (viability) and migration (FIGS. 6E-6H). In addition, knockdown of ZFHX4 induced apoptosis (FIG. 6I).

TDI Reveals Causal Relationship at Individual Tumor Level that Cannot be Detected by Global Causal Analysis.

While it is possible to infer causal relationships between SGAs and DEGs at the cohort level (global) in a similar fashion as the expression quantitative trait loci (eQTL) analysis (Matthew V. Rockman & Leonid Kruglyak, "Genetics of global gene expression", Nature Reviews Genetics 7, 862-872; 2006), global analysis usually prefers the SGAs that are commonly perturbed at the whole cohort level as drivers for DEGs but ignores low-frequency SGAs even though the latter is more specific driver of a DEG. For example, PIK3CA is the $2^{nd}$ most commonly mutated gene in all cancers and a common driver of many cancer process. In global causal analysis, it is deemed as the most probable driver regulating the expression of KLK8, a gene believed to be involved in cancer. KLK8 is differentially expressed 1,497 tumors (out of 4,468 tumors from TCGA) and 34% of these instances is predicted to be caused by SGAs in PIK3CA in global analysis. However, in TDI analysis, PIK3CA is only assigned as driver for KLK8 in 21% of the 1,497 instances, whereas the other 13% instances is assigned to driver SGAs that have lower prevalences in the cohort, including CDKN2A, which is assigned to cause 21% of 1,497 instances of KLK8 DEG events. Interestingly, when SGAs in PIK3CA and CDKN2A co-occur in 87 tumors with differentially expressed KLK8, CDKN2A, rather than PIK3CA, is assigned as the driver of KLK8, indicating that TDI has detected that CDKN2A has a stronger causal relationship with respect to KLK8. The phenomenon can be explained as follows: There is a causal chain PIK3CA→CDKN2A→KLK8. Although CDKN2A is a more direct regulator of KLK8, and it is involved in regulating KLK8 in tumors with PIK3CA, its impact is not observed in those tumors. Since PIK3CA is altered in more tumors than CDKN2A, PIK3CA explains the overall variance of KLK8 in cohort better than CDKN2A, and therefore it is designated as the global driver of KLK8. However, when evaluated at the individual tumor level, TDI can detect that the causal relationship between CDKN2A and KLK8 is stronger than that between PIK3CA and KLK8, due to non-deterministic causal relationship between PIK3CA and CDKN2A, and as such TDI correctly assigns CDKN2A as the driver of KLK8 even though both PIK3CA and CDKN2A are present in a tumor as candidate drivers and that PIK3CA is the global driver. Such results can be detected only by methods that perform instance-based inference such as TDI but not by methods aiming to infer causal relationship at the cohort level. This reflects the key innovation and uniqueness of the TDI algorithm.

TDI Outperforms Conventional Feature Selection Methods in Identifying SGAs that are Predictive of DEG in Tumors.

The disclosed TDI was compared to another alternative approach to identify potential causal relationship between SGAs and DEGs. The alternative approach uses a classification model in combination with a feature-selection method to search for SGAs that are predictive of expression status of a DEG. That is, for each DEG, this approach searches for a set of SGAs that can be used input feature to a classification model to predict the status of the DEG.

Figure 10:
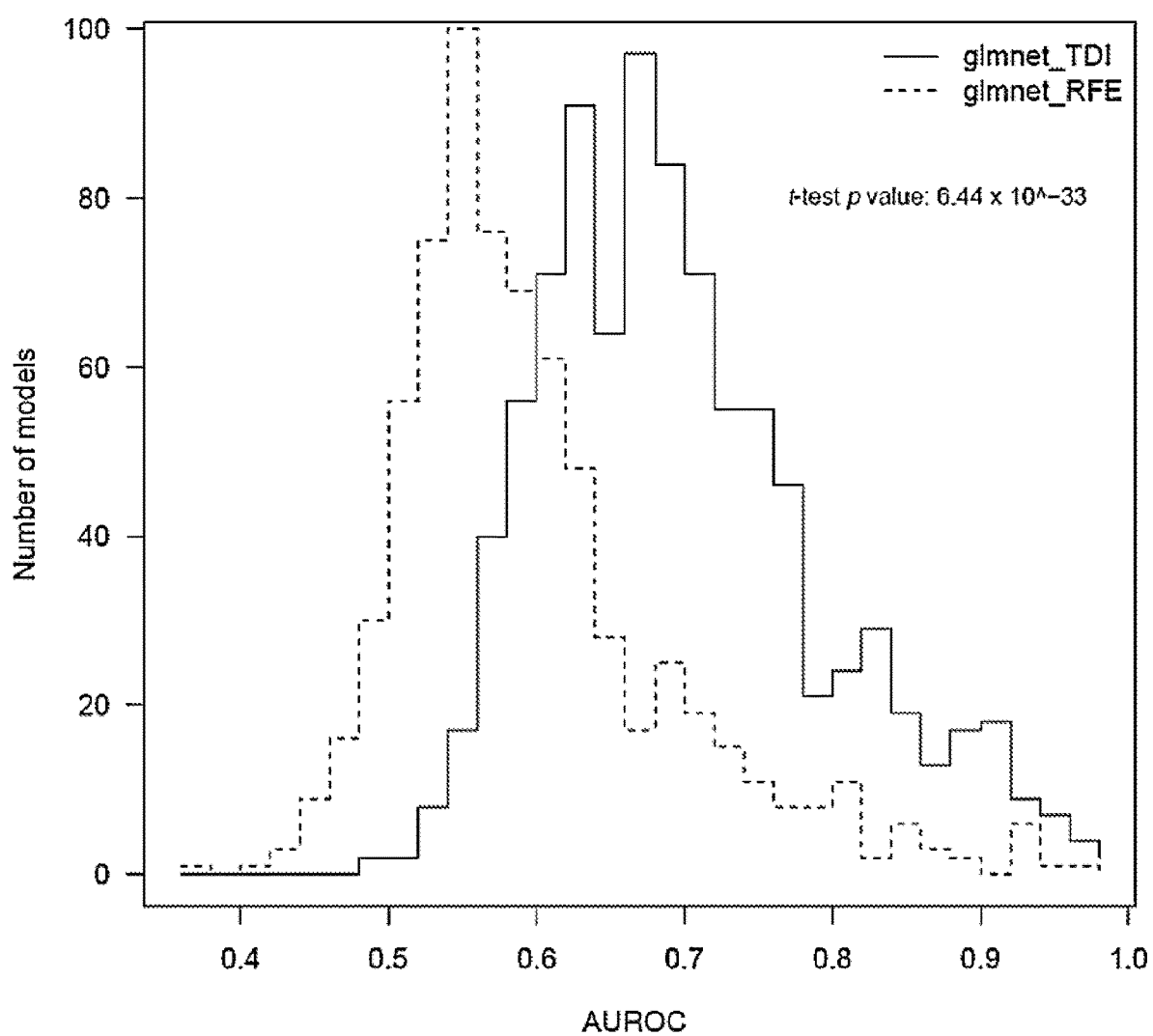
FIG. 10 shows a graph comparing the performances of GLMNET models trained with TDI-derived features and features selected using the RFE algorithm. The x-axis (AU-ROC, area under ROC) represents the area under ROC curve (the higher, the better models perform, with a value of 0.5 indicating performance of random calls); the y-axis represents the number of models within a bin with an AUROC range. Overall performances of two groups of models were compared using t-test, and the p-value of the test is 9.24E-31.

Over 600 DEGs involved in regulating immune responses were selected as target classes; the elastic net model was used as the classification model (implemented in the GLMNET package in R); and the recursive feature elimination (RFE) algorithm was used as the conventional approach to search for informative features. A set of features for each of 600 DEGs was selected and a GLMNET model was trained. The performance of classification model for each DEG was evaluated using the area under the receiver operating curve (AUROC) as the metric. As a comparison, a GLMNET model was also trained for each DEG using the SGAs identified by TDI as input features and their performance was evaluated. FIG. 10 shows that models trained with TDI-derived features significantly outperformed those trained with conventional feature selection and classification methods. These results clearly indicate that the disclosed TDI outperforms conventional methods of studying the relationships between SGAs and DEGs.

DISCUSSION

The TDI algorithm integrates mixed data types to infer causal relationships between SGAs and molecular phenotypes in individual tumors. In general terms, TDI provides a principled statistical framework that can combine multiple genomic and epigenetic alterations as candidate causal events (causes) and use transcriptomic data, proteomic data, and metabolomic data as molecular phenotypes (effects). Thus, TDI combines frequency-oriented information with information about the functional impact to investigate whether the SGAs observed in a single tumor or in a set of tumors contribute to cancer development.

The tumor-specific inference framework enables TDI to delineate the causal relationship between SGAs and DEGs in specific tumors. Other approaches that infer associations between genomic variants and expression changes, such as expression quantitative loci analysis, are not tumor specific, but rather identify functional impact across a set of tumors. However, a DEG can be causally regulated by multiple SGAs perturbing a common pathway in different tumors. For example, genes regulated by the PI3K pathway can be causally affected by SGAs in PIK3CA, PTEN, PIK3R1, and other member genes of the pathway. In such a case, a member gene altered at a relatively low frequency (e.g., PIK3R1) cannot explain the overall variance of a given pathway-regulated DEG at the cohort level. However, in an individual tumor, PIK3R1 may be the only altered member of the PI3K pathway and may therefore account for the PI3K-regulated DEGs in the tumor better than other SGAs. A strength of TDI is its ability to designate PI3K the major cause of the DEG with high confidence. Indeed, TDI offers more globally a general approach to case-specific inference that can build causal models between perturbations and responses in any biological system at the individual case level, be it a person, organ, tissue, or cell. Furthermore, as shown above, TDI outperforms conventional methods of studying the relationships between SGAs and DEGs.

Methods

SGA Data Collection and Preprocessing.

SM data for 16 cancer types were obtained directly from the TCGA data matrix portal (tcga-data.nci.nih.gov/tcga/dataAccessMatrix.htm). All the non-synonymous mutation events of all genes were considered at the gene level, where a mutated gene is defined as one that contains one or more non-synonymous mutations or indels.

SCNA data (processed using GISTIC2) were obtained from the Firehose browser of the Broad Institute (gdac.broadinstitute.org). The TCGA network employed GISTIC 2.0 to process SCNA data, which discretized the gene SCNA into five different levels: homozygous deletion, single copy deletion, diploid normal copy, low copy number amplification, and high copy number amplification. Only genes with homozygous deletion or high copy number amplification were included for further analysis. Additionally, genes with inconsistent copy number variations across tumors in a given cancer type were screened out. More specifically, if a gene is perturbed by both copy number amplification and deletion events in a cancer type, and both types of events have a prevalence>25% of tumors, the gene is deemed to be affected by insistent SCNA events, and it is excluded from further analysis.

Preprocessed SM data and SCNA data were combined as SGA data, such that a gene in a given tumor is designated as altered if it is affected by either an SM or an SCNA event or by both. Since certain recurrent SCNAs enclose multiple genes whose alteration events are inseparable, neighboring genes were organized into an SGA unit by first identifying a pair of genes that are co-perturbed 90% of the time in all instances, followed by greedily including a neighbor gene if it is also co-perturbed 90% of the time with the boundary gene.

DEG Data Collection and Preprocessing.

Gene expression data were preprocessed and obtained from the Firehose browser of the Broad Institute. We used RNASeqV2 for cancer types with expression measurements in normal tissues. For cancer types without RNASeqV2 measurements in normal cells (i.e., GBM and OV), we used microarray data to identify DEGs. We determined whether a gene is differentially expressed by comparing the gene expression in the tumor cell against that in the corresponding tissue-specific normal cells. For a given cancer type, assuming the expression of each gene follows Gaussian distribution in normal cells, we calculated the p values of each gene in a tumor which estimated how significant the gene expression in tumor is different from those of normal cells. If the p value was equal or smaller than 0.005 to either side, the gene was considered as differentially expressed in the corresponding tumor. For genes whose expression do not follow Gaussian distribution in normal samples due to low variance (i.e., <0.1), we calculated the expression folder change for those genes (i.e., the gene expression in the tumor cell over the average gene expression in normal cells) and set 3 fold changes as the threshold to determine the DEGs in the tumor cell.

We used a 3-fold change cutoff, because it represents a stringent threshold to determine a gene-expression on/off state. By applying both p value calculations and 3-fold change calculations to the genes whose expression follows a Gaussian distribution in normal samples, we found that over 80% of the DEG events identified using fold changes are also recovered using significant p values of 0.5%. Furthermore, if a gene expression up-regulation co-occurs with its corresponding copy number amplification or a gene expression down-regulation co-occurs with its corresponding copy number deletion, we removed it from the DEG list of the tumor, because its differential expression is more likely due to copy number alteration rather than dysregulation. Moreover, we removed tissue specific DEGs if they are highly correlated with cancer types or tissue origin (i.e., Pearson correlation coefficient larger than 0.9). Therefore, we identified the DEGs for each tumor and created a tumor-gene binary matrix where 1 represents expression change and 0 represents no expression change.

TDI Method

The TDI method was designed to infer the functional-impact relationships between SGAs and DEGs for a given tumor using a CBN, in which causal edges are only allowed to point from SGAs to DEGs. It was assumed that each DEG is likely regulated by one aberrant pathway in an individual tumor and that such a pathway is likely perturbed by a single SGA due to the well known mutual exclusivity among SGAs perturbing a common pathway. Let $T=\{T_1, T_2, \ldots, T_t, \ldots, T_N\}$ denote the tumor set which contains a total of N tumor samples, where t indexes over the tumors included in the tumor set. Let $SGA\_SET_t=\{A_1, A_2, \ldots, A_h, \ldots, A_m\}$ denote a subset of m genes with genome alterations in tumor t (i.e., the SGAs) and let h indexes over the variables in $SGA\_SET_t$. Let $DEG\_SET_t=\{E_1, E_2, \ldots, E_i, \ldots, E_n\}$ denote n genes that are differentially expressed in tumor t, and let i index over the variables in $DEG\_SET_t$ (i.e., the DEGs). A variable $A_0$ was further included to collectively represent factors other than SGAs (e.g., tumor microenvironment) that may affect the gene expression. Therefore, for a tumor t, the TDI method searches for a CBN model M that best explains the data and assigns one $A_h$ in $SGA\_SET_t$ as the most probable cause for each $E_i$ in $DEG\_SET_t$. In model M, a given $A_h$ can have zero, one, or more arcs emanating from it to the variables in $DEG\_SET_t$. For each tumor from the TCGA dataset (D), TDI searches for the CBN with a maximal posterior probability based on Bayes rule:

$$P(M|D) = \frac{P(D,M)}{P(D)} = \frac{P(D|M)P(M)}{\sum_{m'} P(D|M')P(M')} \quad (1)$$

where P(D|M) is the marginal likelihood of causal network structure M, and P(M) is the prior probability of M.

The tumor-specific nature of the TDI method is reflected in the following aspects: 1) Each tumor has a unique $SGA\_SET_t$ and the $DEG\_SET_t$; thus, the TDI method inferred CBN structure M is tumor-specific. 2) The prior probability of a model (M) (i.e., $(A_h \to E_i)$) is tumor-specific. 3) Calculation of the marginal likelihood $(D|A_h \to E_i)$ consists of two components: one component is computed using the data from the tumors with $A_h=1$, (a.k.a., "tumors like me"), and the other component is derived using a global model. As such, the posterior probability of the edge $A_h \to E_i$ is specific to a given tumor, and the same edge $A_h \to E_i$ may have different posterior probabilities in different tumors depending on the composition of $SGA\_SET_t$.

Tumor-Specific Model Priors P(M).

Assuming the structure prior is modular, we factorize the probability P(M) as a product of prior probabilities for each edge included in M, i.e., $P(M)=\Pi_{i=1}^n \Pi_{h=0}^m P(A_h \to E_i)$. While it would be ideal to define the prior probability for each edge $(A_h \to E_i)$ using specific prior knowledge, we usually have very limited information about it. Despite of the lack of specific prior knowledge, we derive the prior probability P(M) by incorporating well-appreciated general knowledge (which the frequency-oriented approaches are based on) regarding the probability that a gene is a driver: the more frequently a gene is perturbed in a cancer cohort, the more likely it is a driver in an individual tumor. Furthermore, we also consider the tumor-specific context of the SGAs in each tumor.

We designed a Bayesian method that incorporates all the above considerations. For a tumor t and an arbitrary DEG $E_i$, we defined the prior probability of $A_h$ being a parent of $E_i$ using a multinomial distribution with a parameter vector $\theta=(\theta_0, \theta_1, \theta_2; \ldots, \theta_h, \ldots, \theta_m)^T$, where $\Sigma_{j=0}^m \theta_h=1$. Here, $\theta_0$ is a user-defined parameter representing the prior belief that the non-SGA factor $A_0$ is the cause of $E_i$, and $\theta_h$ represents the prior probability of $A_h$ being the cause of $E_i$. We assumed that $\theta$ is distributed as $(\theta|\mu)$, where $\mu=(\mu_0, \mu_1, \ldots, \mu_h, \ldots, \mu_m)^T$ is a tumor specific Dirichlet parameter vector governing the distribution of $\theta$ in a tumor t. For a tumor t, we calculated the prior probability $\theta_h$ as follows:

$$\theta_h = (1-\theta_0) \frac{\mu_h}{\sum_{h'=1}^m \mu'_h} \quad (2)$$

where h' indexes over the m variables in $SGA\_SET_t$, $$\mu_h = \sum_{t' \in U_h} \frac{1}{m_{t'}}$$

is a Drichlet parameter, $U_h$ denotes tumor genomes in a reference set of tumor genomes, D, for which $A_h=1$, and me denotes the number of variables in $SGA\_SET_{t'}$ for tumor t'.

When additional genomic information, such as the number of unique synonymous mutations in a particular gene in a reference set of tumor genomes D and the number of somatic copy number alterations in the particular gene in subjects without cancer, was available for each gene $A_h$, we applied the additional genomic information to account for mutation and copy number alterations that are due to differences in gene lengths and chromosome locations and derive alternative versions of $\mu_h$. Thus, where the number of unique synonymous mutations in gene $A_h$ in a reference set of tumor genomes, D, has a known value (a1); and the number of somatic copy number alterations in gene $A_h$ in subjects without cancer has a known value (a2), $\mu_h$ is calculated as:

$$\Sigma_{t' \in U_h} w_{ht'}$$

wherein $U_h$ denotes tumor genomes from a reference set of tumor genomes, D, that have a somatic alteration in gene $A_h$; $M_{t'}$ denotes the number of genes with SGAs in the genome of tumor t', and $w_{ht'}$ denotes a weight proportional to the probability that the somatic alteration in gene $A_h$ is the SGA with functional impact in the genome of tumor t'. $w_{ht'}$ is calculated as:

$$w_{ht'} = \frac{R_{ht'}}{\sum_{h'=1}^{m} R_{h't'}},$$

wherein $$R_{ht'} = \frac{T_{ht'}^{SM}}{R_h^{SM}} + \frac{T_{ht'}^{SCNA}}{R_h^{SCNA}}.$$

In the above equations, $T_{ht'}^{SM}$ denotes whether gene $A_h$ has a non-synonymous somatic mutation or not in tumor t' (e.g., $T_{ht'}^{SM}$ can be 1 or 0, respectively); $R_h^{SM}$ denotes the number of unique synonymous somatic mutation events in gene $A_h$ in the reference set of tumor genomes, D; $T_{ht'}^{SCNA}$ denotes whether gene $A_h$ has a somatic copy number alteration or not in tumor t' (e.g., $T_{ht'}^{SCNA}$ is 1 or 0, respectively); $R_h^{SCNA}$ denotes the expected number of times gene $A_h$ has a somatic copy number alteration among the tumors in D, and yet is only a passenger alteration (that is, has no functional impact), based on the number of times gene $A_h$ has a somatic copy number alteration in a reference set of genomes from subjects without known cancer (e.g., subjects in the normal human population).

Marginal Likelihood Function P(D|M).

The specifications of the TDI method allow decomposition of the marginal likelihood of a model M to be a product of the marginal likelihoods of all edges in M. We used the Bayesian BDeu scoring measure to derive P(D|M) in closed form:

$$P(D \mid M) = \qquad (3)$$

$$\int P(D \mid M, \theta) P(\theta \mid M) d\theta = \prod_{i=1}^{n} \prod_{j=1}^{q_i} \frac{\Gamma(\alpha_{ij})}{\Gamma(\alpha_{ij} + N_{ij})} \prod_{k=1}^{r_i} \frac{\Gamma(\alpha_{ijk} + N_{ijk})}{\Gamma(\alpha_{ijk})}$$

where $\theta$ denotes parameters of the model M; j indexes over the states of $A_h$, which is being considered as the cause of $E_i$; $q_i$ is the number of possible values of $A_h$ (in our case, it is 2, because $A_h$ is modeled as a binary variable); k is an indicator variable which indexes over the states of $E_i$, and $r_i$ denotes the total possible states of $E_i$ (in our case, it is set to 2); $N_{ijk}$ is the number of tumors in D that node $E_i$ has value k and its cause has the value denoted by j; $\alpha_{ijk}$ is a parameter in a Dirichlet distribution that represents prior belief about $P(E_i=k|\text{cause}(E_i)=j)$; $\Gamma$ is the gamma function; $N_{ij}=\Sigma_{k=1}^{r_i} N_{ijk}$; $\alpha_{ij}=\Sigma_{k=1}^{r_i} \alpha_{ijk}$. Let e(h, i) represent the function that calculate the Bayesian score of the edge $A_h \rightarrow E_i$ in tumor t. Then, e(h, i) can be defined as follows:

$$e(h, i) = \theta_h \prod_{j=1}^{q_i} \frac{\Gamma(\alpha_{ij})}{\Gamma(\alpha_{ij} + N_{ij})} \prod_{k=1}^{r_i} \frac{\Gamma(\alpha_{ijk} + N_{ijk})}{\Gamma(\alpha_{ijk})}. \qquad (4)$$

The tumor-specific calculation of the marginal likelihood is to use the data that are most relevant to the given tumor (aka "tumors like me") to infer if the hypothesis of a candidate causal edge $A_h \rightarrow E_i$ is supported among these tumors. To this end, we modified the Bayesian scoring function (Eq (3)) by dividing the training data D into a tumor-specific subset (the subset of tumors with $A_h=1$) and a global training set (the subset in which variance of $E_i$ is explained by a global cause). Let $D_h^1$ denote the subset of tumors in which $A_h=1$ and $D_h^0$ denote the subset of tumors in which $A_h=0$, such that $D=\{D^0 \cup D^1\}$. Let G(i) represent the SGA with maximal Bayesian score for $E_i$ derived from Eq (4) at the whole cohort level (where G(i) is referred to as the "global driver"), and let $\theta_{G(i)}$ denote the prior probability of G(i) as the cause for any $E_i$ in tumor t. We can calculate the $e(h, i, D_h^1)$ and $e(G(i), i, D_h^0)$ for tumor set with $A_h=1$ and those with $A_h=0$ respectively as follows, $$e(h, i, D_h^1) = \theta_h \prod_{j=1}^{q_i} \frac{\Gamma(\alpha_{ij})}{\Gamma(\alpha_{ij} + N_{ij}^1)} \prod_{k=1}^{r_i} \frac{\Gamma(\alpha_{ijk} + N_{ijk}^1)}{\Gamma(\alpha_{ijk})} \qquad (5)$$

$$e(G(i), i, D_h^0) = \theta_{G(i)} \prod_{j=1}^{q_i} \frac{\Gamma(\alpha_{ij})}{\Gamma(\alpha_{ij} + N_{ij}^0)} \prod_{k=1}^{r_i} \frac{\Gamma(\alpha_{ijk} + N_{ijk}^0)}{\Gamma(\alpha_{ijk})} \qquad (6)$$

$$e(h, i) = e(h, i, D_h^1) * e(G(i), i, D_h^0) \qquad (7)$$

where $N_{ijk}^1$ is the number of tumors in $D_h^1$ that $E_i$ has value k and $A_h$ has the value indexed by j; $N_{ijk}^0$ is the number of tumors in $D_h^0$ that $E_i$ has value k and $A_{G(i)}$ has the value indexed by j. Finally, the posterior probability of a causal edge $A_h \rightarrow E_i$ can be calculated with the following equation:

$$P(A_h \rightarrow E_i \mid D, \text{SGA\_SET}_t, \text{DEG\_SET}_t) = \frac{e(h, i)}{\sum_{h'=0}^{m} e(h', i)} \qquad (8)$$

Identification of SGA-FIs.

Figure 9:
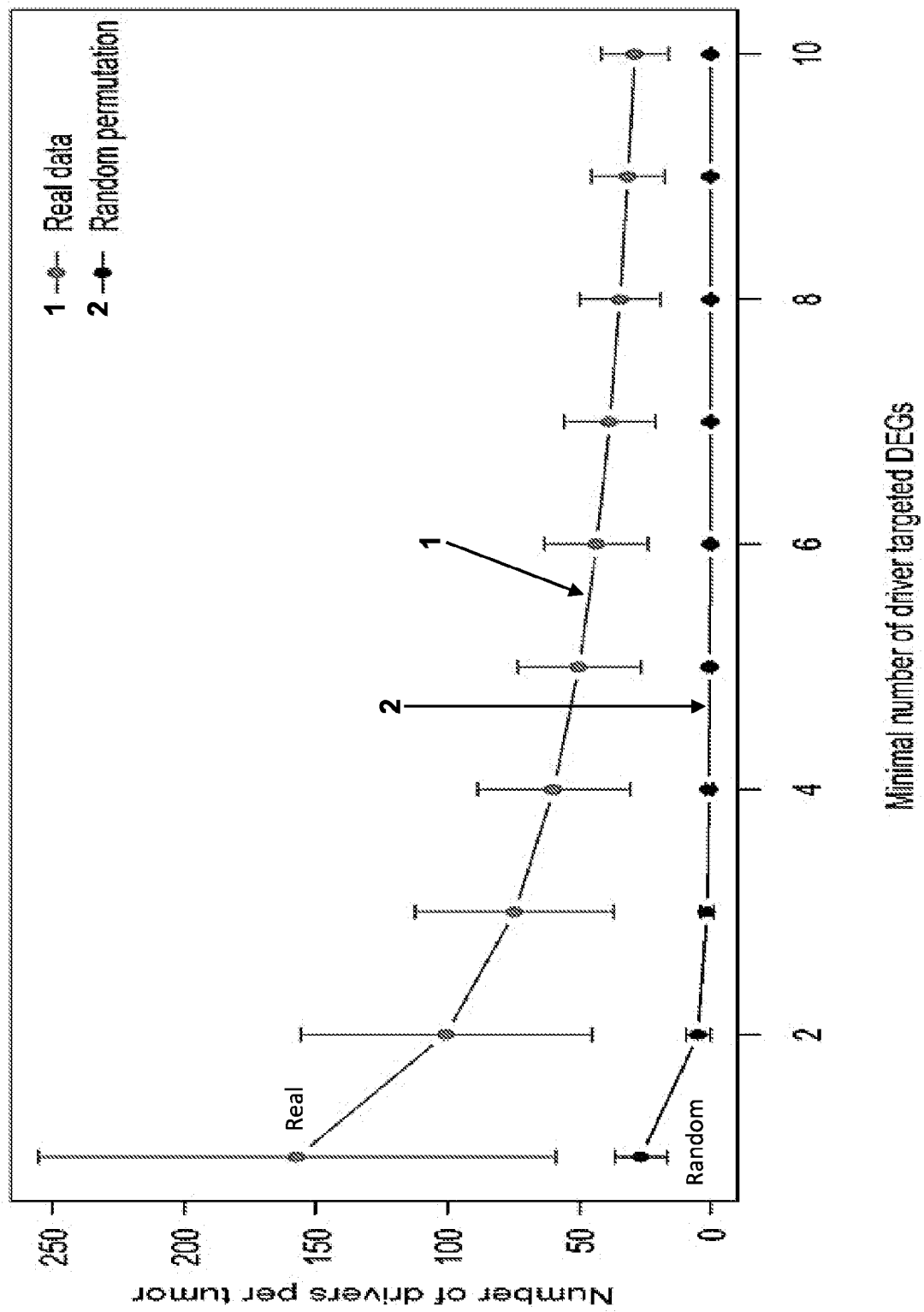
FIG. 9 is a graph illustrating the false discovery rate using the TDI method. The plot shows the relationship of number of SGAs per tumor being designated as SGA-FIs (drivers) with respect to the minimal number of targeted (caused) DEGs an SGA-FI must have. Results are shown for random and real data. The x-axis shows the different thresholds, i.e., the number of DEGs predicted to be regulated by an SGA with $p<0.001$, and the y-axis shows the number of SGAs designated as SGA-FI in a tumor.

Causal edges from different SGAs have different posterior probabilities, as expected. To standardize how to interpret the significance of an edge probability $P_e$, a method was developed that uses a permutation test to determine the probability that an edge from an SGA can be assigned with a given $P_e$ or higher in data from permutation experiments, i.e., the p value to the edge with a given $P_e$. The p value in this setting is also the expected rate of false discovery of an SGA as the cause of a DEG by random chance. A series of experiments was performed, in which the values of DEGs were permuted across tumors, so that the statistical relationship in real data was disrupted, and then TDI was applied to both random and real datasets to evaluate the extent to which a random sample can lead to the false discovery of causal relationships. As FIG. 9 shows, no SGA was designated as an SGA-FI in the random dataset (when the number of driver targeted DEGs was 5 or greater), indicating that the false discovery is well controlled. Therefore, this property was utilized to control the false discovery when identifying SGA-FIs in a tumor. An SGA event in a tumor was designated as an SGA-FI if it has 5 or more causal edges to DEGs that are each assigned a p-value<0.001. The overall false discovery rate of the joint causal relationships between an SGA to 5 or more target DEGs is less than or equal to $10^{-15}$.

Cell Culture and siRNA Transfection.

HGC27 (Sigma-Aldrich) and PC-3 (ATCC) cells were cultured according to the manufacturer's recommendations. The non-targeting and the CSMD3 and ZFHX4 siRNAs were obtained from OriGene (Rockville, MD). The siRNA sequences are as follows:

```
si-CSMD3-1,
                              (SEQ ID NO: 1)
GGUAUAUUACGAAGAAUUGCAGAGT si-CSMD3-2,
                              (SEQ ID NO: 2)
ACAAAUGGAGGAAUACUAACAACAG si-ZFHX4-1,
                              (SEQ ID NO: 3)
CGAUGCUUCAGAAACAAAGGAAGAC si-ZFHX4-2,
                              (SEQ ID NO: 4)
GGAACGACAGAGAAAUAAAGAUUCA
```

The siRNAs were transfected into cells using DharmaFECT transfection reagents for 48 hrs according to the manufacturer's instructions.

RNA Extraction and Real Time RT-qPCR.

Total RNA for cells was extracted using RNeasy® Mini kit (Qiagen, USA) following standard procedures. One microgram of total RNAs was used to generate cDNA using the iScript™ cDNA synthesis kit. Real-time PCR was subsequently performed using the iTaq™ Universal SYBR® Green Supermix (Bio-Rad) on the CFX96™ Real-Time PCR Detection System (Bio-Rad, Richmond, CA, USA). Data were normalized using ribosomal protein L37A (RPL37A) as an internal control.

Cell Proliferation and Viability Assays.

Cell proliferation/viability was assayed by CCK-8 assay (Dojindo Laboratories, Kumamoto, Japan). Briefly, HGC27 and PC3 cells were plated at a density of $3\times10^3$ cells/well in 96-well plates. After siRNA transfection for 3 or 6 days, CCK-8 solution containing a highly water-soluble tetrazolium salt WST-8 [2-(2-methoxy-4-nitrophenyl)-3-(4-nitrophenyl)-5-(2,4-disulfophenyl)-2H-tetrazolium, monosodium salt] was added to cells in each well, followed by incubation for 1-4 h. Cell viability was determined by measuring the O.D. at 450 nm. Percent over control was calculated as a measure of cell viability.

Transwell Migration Assay.

Cell migration was measured using 24-well transwell chambers with 8 μm pore polycarbonate membranes (Corning, Corning, NY). SiRNA-transfected cells were seeded at a density of $7.5\times10^4$ cells/ml to the upper chamber of the transwell chambers in 0.5 ml growth media with 0.1% FBS. The lower chamber contained 0.9 ml of growth medium with 20% FBS as chemoattractant media. After 20 hrs of culture, the cells in the upper chamber that did not migrate were gently wiped away with a cotton swab, the cells that had moved to the lower surface of the membrane were stained with crystal violet and counted from five random fields under a light microscope.

Apoptotic Assay.

Apoptosis was assessed by flow cytometry analysis of annexin V and propidium iodide (PI) double stained cells using Vybrant Apoptosis Assay Kit (Thermo Fisher Scientific, Carlsbad, CA). Briefly, the cells after washing with PBS were incubated in annexin V/PI labeling solution at room temperature for 10 min, then analyzed in the BD FACSCalibur flow cytometer (Becton, Dickinson and Company, Franklin Lakes, NJ).

In view of the many possible embodiments to which the principles of the disclosed technology may be applied, it should be recognized that the illustrated embodiments are only preferred examples and should not be taken as limiting the scope of the disclosure. Rather, the scope of the disclosure is at least as broad as the following claims. We therefore claim all that comes within the scope of the following claims.

---

It is claimed:

1. A method for detecting a somatic genome alteration (SGA) with tumor-specific functional impact in a genome of a specific tumor t of a subject, comprising:
   receiving a training dataset that comprises gene expression data indicating respective levels of expression of a plurality of genes in a collection of tissue samples including tumors;
   receiving a set of SGAs in the genome of t;
   training a bipartite causal Bayesian network (CBN) with maximal posterior probability, including:
      identifying a set of differentially expressed genes (DEGs) in the genome of t by designating each gene in a set of genes in the genome of t as a DEG if the respective level of expression of the gene in t falls outside a significance boundary determined based on respective levels of expression of the gene in the collection of tissue samples represented in the training dataset;
      for each DEG in the set of DEGs:
         (i) identifying, from among multiple SGAs in the set of SGAs that are possible causes of the DEG, one SGA that is the most probable cause of the DEG, and
         (ii) providing the DEG with just a single causal edge in the CBN with maximal posterior probability, the single causal edge connecting the DEG in the CBN to the SGA that has been identified as the most probable cause of the DEG, wherein the DEG is not connected in the CBN to any other SGAs except for the SGA that has been identified as the most probable cause of the DEG; and
   identifying a particular SGA that is connected by respective causal edges to at least a threshold number of DEGs in the CBN with maximal posterior probability as the SGA with tumor-specific functional impact in the genome of t.

2. The method of claim 1, wherein training the CBN with maximal posterior probability comprises:
   generating a plurality of test CBNs for the set of SGAs and the set of DEGs, determining a posterior probability for each test CBN in the plurality of test CBNs, and identifying the test CBN with the maximal posterior probability.

3. The method of claim 2, wherein determining the posterior probability for a test CBN in the plurality of test CBNs comprises calculating P(D|M)×P(M), wherein:
   P(D|M) is a marginal likelihood of the test CBN; and
   P(M) is a prior probability of the test CBN.

4. The method of claim 3, wherein P(M) comprises a product of the frequencies at which the SGAs of the test CBN are present in a reference set of tumor genomes, D.

5. The method of claim 3, wherein P(D|M) comprises a product of marginal likelihoods of causal edges of the test CBN for tumor t.

6. The method of claim 3, wherein P(D|M) comprises a product of posterior probabilities of causal edges of the test CBN, and calculating said product comprises:
   calculating a posterior probability of each causal edge $A_h \rightarrow E_i$ of the CBN as:

$$\frac{e(h, i)}{\sum_{h'=0}^{m} e(h', i)}$$

wherein:

$$e(h, i) = e(h, i, D_h^1) \cdot e(G(i), i, D_h^0)$$

$$e(h, i, D_h^1) = \theta_h \prod_{j=1}^{q_i} \frac{\Gamma(\alpha_{ij})}{\Gamma(\alpha_{ij} + N_{ij}^1)} \prod_{k=1}^{r_i} \frac{\Gamma(\alpha_{ijk} + N_{ijk}^1)}{\Gamma(\alpha_{ijk})}$$

$$e(G(i), i, D_h^0) = \theta_{G(i)} \prod_{j=1}^{q_i} \frac{\Gamma(\alpha_{ij})}{\Gamma(\alpha_{ij} + N_{ij}^0)} \prod_{k=1}^{r_i} \frac{\Gamma(\alpha_{ijk} + N_{ijk}^0)}{\Gamma(\alpha_{ijk})}$$

wherein:
   $D_h^1$ denotes tumor genomes having the somatic alteration of gene $A_h$ that are present in D,
   $D_h^0$ denotes tumor genomes that do not have the somatic alteration of gene $A_h$ that are present in D;
   G(i) denotes a gene that has a maximal posterior probability for causing $E_i$ in D, which is calculated by finding the gene g that maximizes the following function and assigning G(i) to be g:

$$\theta_g \prod_{j=1}^{q_i} \frac{\Gamma(\alpha_{ij})}{\Gamma(\alpha_{ij} + N_{ij})} \prod_{k=1}^{r_i} \frac{\Gamma(\alpha_{ijk} + N_{ijk})}{\Gamma(\alpha_{ijk})}$$

wherein
- $N_{ijk}$ is the number of tumor genomes in D, wherein node $E_i$ has value k and its modeled cause $A_g$ has the value denoted by j, and
- $\theta_g$ denotes the prior probability that $A_g$ is the cause for $E_i$ for the tumor genomes D; and
- j indexes over the states of $A_g$, which is being considered as the cause of $E_i$;
- $q_i$ is 2;
- k is an indicator variable which indexes over the states of $E_i$;
- $r_i$ is 2;
- $\alpha_{ijk}$ is a parameter in a Dirichlet distribution that is proportional to the prior probability of $P(E_i=k|A_g=j)$;
- $\Gamma$ is the gamma function;
- $N_{ij} = \Sigma_k^{r_i} N_{ijk}$;
- $\alpha_{ij} = \Sigma_k^{r_i} \alpha_{ijk}$;
- $N_{ijk}^1$ is the number of tumor genomes in $D_h^1$ for which $E_i$ has value k and $A_h$ has the value indexed by j;
- $N_{ijk}^0$ is the number of tumor genomes in $D_h^0$ for which $E_i$ has value k and $A_{G(i)}$ has the value indexed by j;

and wherein $$\theta_h = (1 - \theta_0) \frac{\mu_h}{\sum_{h'=1}^{m} \mu_{h'}}$$

wherein:
- $\theta_0$ is a prior probability that something other than a SGA is the cause of DEG $E_i$;
- h' indexes over the number m of genes in tumor t that have SGAs in gene h'; and
- $\mu_g$ is a Dirichlet parameter set forth as $$\sum_{t' \in U_h} \frac{1}{m_{t'}}$$

or $$\sum_{t' \in U_h} w_{ht'}$$

wherein $U_g$ denotes tumor genomes from a reference set of tumor genomes, D, that have a somatic alteration in gene $A_g$; $m_{t'}$ denotes the number of genes with somatic alterations in the genome of tumor t', and $w_{gt'}$ denotes a weight proportional to the probability that the somatic alterations in gene $A_g$ is the SGA with functional impact in the genome of tumor t'.

7. The method of claim 6, wherein
$w_{gt'}$ is set forth as:

$$\frac{R_{ht'}}{\sum_{h'=1}^{m} R_{h't'}},$$

$R_{gt'}$ is set forth as:

$$\frac{T_{gt'}^{SM}}{R_g^{SM}} + \frac{T_{gt'}^{SCNA}}{R_g^{SCNA}};$$

and wherein:
- $T_{gt'}^{SM}$ denotes whether gene $A_g$ has a non-synonymous somatic mutation or not in tumor t';
- $R_g^{SM}$ denotes the number of unique synonymous mutations in gene $A_g$ in the reference set of tumor genomes, D;
- $T_{gt'}^{SCNA}$ denotes whether gene $A_g$ has a somatic copy number alteration or not in tumor t'; and
- $R_g^{SCNA}$ denotes an expected number of times that gene $A_g$ has a somatic copy number alteration without a functional impact in the reference set of tumor genome, D, based on a corresponding number of times that gene $A_g$ has a somatic copy number alteration in a reference set of genomes from subjects without known cancer.

8. The method of claim 1, wherein the SGAs in the set of SGAs comprise or consist of somatic mutations and somatic copy number alterations.

9. The method of claim 1, wherein the genes in the set of DEGs comprise:
- genes of the tumor genome with an RNA expression level having a p-value of 0.005 or less for a Gaussian distribution of control RNA expression levels of corresponding genes in non-tumor tissue; and/or
- genes of the tumor genome with a 3-fold or greater change in RNA expression level compared to control RNA expression levels of corresponding genes in non-tumor tissue.

10. The method of claim 1, further comprising:
- obtaining a tumor sample from the subject, the tumor sample obtained from the specific tumor t;
- identifying DEGs in the genome of the tumor sample; and
- identifying SGAs in the genome of the tumor sample to provide the set of SGAs and the set of DEGs.

11. The method of claim 1, wherein the particular SGA with tumor-specific functional impact is a driver SGA.

12. The method of claim 1, treating the specific tumor t of the subject with a molecularly targeted therapy, the molecularly targeted therapy selected to treat the specific tumor t based on an outcome or a sensitivity of the molecularly targeted therapy determined based on the particular SGA that was identified as having tumor-specific functional impact with respect to t.

13. The method of claim 1, wherein the threshold number is five.

14. One or more computer-readable media comprising computer-executable instructions that when executed cause a computing system to perform operations for detecting a somatic genome alteration (SGA) with tumor-specific functional impact in a genome of a specific tumor t, the operations comprising:
- receiving a training dataset that comprises gene expression data indicating respective levels of expression of a plurality of genes in a collection of tissue samples including tumors;
- receiving a set of SGAs in the genome of t;
- training a bipartite causal Bayesian network (CBN) with maximal posterior probability, including:
  - identifying a set of differentially expressed genes (DEGs) in the genome of t by designating each gene in a set of genes in the genome of t as a DEG if the respective level of expression of the gene in t falls outside a significance boundary determined based on respective levels of expression of the gene in the collection of tissue samples represented in the training dataset; and for each DEG in the set of DEGs:
(i) identifying, from among multiple SGAs in the set of SGAs that are possible causes of the DEG, one SGA that is the most probable cause of the DEG, and
(ii) providing the DEG with just a single causal edge in the CBN with maximal posterior probability, the single causal edge connecting the DEG in the CBN to the SGA that has been identified as the most probable cause of the DEG, wherein the DEG is not connected in the CBN to any other SGAs except for the SGA that has been identified as the most probable cause of the DEG; and identifying a particular SGA that is connected by respective causal edges to at least a threshold number of DEGs in the CBN with maximal posterior probability as the SGA with tumor-specific functional impact in the genome of t.

15. The one or more computer-readable media of claim 14, wherein the operations comprise predicting an outcome or a sensitivity of a molecularly targeted therapy for treatment of t based on the particular SGA that was identified as having tumor-specific functional impact with respect to t.

16. A computing system, comprising:
one or more processors;
memory; and
a classification tool configured to perform operations for detecting a somatic genome alteration (SGA) with tumor-specific functional impact in a genome of a specific tumor t:
receive a training dataset that comprises gene expression data indicating respective levels of expression of a plurality of genes in a collection of tissue samples including tumors;
receive a set of SGAs in the genome of the specific tumor t;
train a bipartite causal Bayesian network (CBN) with maximal posterior probability, including:
(i) identify a set of differentially expressed genes (DEGs) in the genome of t by designating each gene in a set of genes in the genome of t as a DEG if the respective level of expression of the gene in t falls outside a significance boundary determined based on respective levels of expression of the gene in the collection of tissue samples represented in the training dataset; and
(ii) for each DEG in the set of DEGs:
(a) identify, from among multiple SGAs in the set of SGAs that are possible causes of the DEG, one SGA that is the most probable cause of the DEG, and
(b) provide the DEG with just a single causal edge in the CBN with maximal posterior probability, the single causal edge connecting the DEG in the CBN to the SGA that has been identified as the most probable cause of the DEG, wherein the DEG is not connected in the CBN to any other SGAs except for the SGA that has been identified as the most probable cause of the DEG; and
(c) classify one or more of the SGAs from which at least a threshold number of causal edges in the CBN connect to DEGs as SGAs with tumor-specific functional impact, wherein the threshold number of causal edges of each of the one or more SGAs indicate that the SGA is the most probable cause of five or more respective DEGs.

17. The computing system of claim 16, wherein the classification tool is further configured to generate the CBN with maximal posterior probability by:
generating a plurality of test CBNs for the set of SGAs and the set of DEGs;
determining a posterior probability for each test CBN in the plurality of test CBNs; and
identifying the test CBN with the maximal posterior probability.

18. The computing system of claim 17, wherein the classification tool is further configured to determine the posterior probability for each test CBN in the plurality of test CBNs by calculating $P(D|M) \times P(M)$, wherein:
$P(D|M)$ is a marginal likelihood of the test CBN; and
$P(M)$ is a prior probability of the test CBN.

19. The computing system of claim 18, wherein $P(M)$ comprises a product of the frequencies at which the SGAs of the test CBN are present in a reference set of tumor genomes, D.

20. The computing system of claim 16, wherein the classification tool is further configured to predict an outcome or a sensitivity of a molecularly targeted therapy for treatment of t based on the one or more of the SGAs that are classified as having tumor-specific functional impact.

* * * * *